US 8,163,713 B2

United States Patent
Nishizawa et al.

(10) Patent No.: US 8,163,713 B2
(45) Date of Patent: Apr. 24, 2012

(54) TREHALOSE COMPOUND AND PHARMACEUTICAL COMPRISING THE COMPOUND

(75) Inventors: Mugio Nishizawa, Tokushima (JP); Hiroshi Imagawa, Tokushima (JP); Hirofumi Yamamoto, Tokushima (JP)

(73) Assignee: Otsuka Chemical Co., Ltd., Osaka-shi (JP)

( * ) Notice: Subject to any disclaimer, the term of this patent is extended or adjusted under 35 U.S.C. 154(b) by 663 days.

(21) Appl. No.: 12/294,800

(22) PCT Filed: Mar. 22, 2007

(86) PCT No.: PCT/JP2007/055834
§ 371 (c)(1),
(2), (4) Date: Jan. 23, 2009

(87) PCT Pub. No.: WO2007/111214
PCT Pub. Date: Oct. 4, 2007

(65) Prior Publication Data
US 2010/0249057 A1    Sep. 30, 2010

(30) Foreign Application Priority Data
Mar. 27, 2006 (JP) .................................. 2006-85245

(51) Int. Cl.
A61K 31/70 (2006.01)
C07H 13/02 (2006.01)
(52) U.S. Cl. ......................................... 514/53; 536/119
(58) Field of Classification Search ............ 536/119
See application file for complete search history.

(56) References Cited

U.S. PATENT DOCUMENTS

| | | | |
|---|---|---|---|
| 5,049,664 A | 9/1991 | Yoshinaga et al. | 536/119 |
| 2002/0058067 A1 | 5/2002 | Blair | 424/484 |
| 2005/0101551 A1 | 5/2005 | Sevillano et al. | 514/43 |

FOREIGN PATENT DOCUMENTS

| | | |
|---|---|---|
| JP | 03-047193 | 2/1991 |
| JP | 11-158073 | 6/1999 |
| JP | 11-171727 | 6/1999 |
| JP | 2001-527087 | 12/2001 |
| JP | 2003-519102 | 6/2003 |
| JP | 2006-502088 | 1/2006 |

OTHER PUBLICATIONS

Prome, J.-C., et al., Field Desorption of Oligosaccharides and Glycolipids by the Cationization Method, Israel Journal of Chemistry, 1978, vol. 17. No. 3, pp. 172-176, see p. 3 of specification.
Y. Kasahara, et al., Colorimetry of Angiotensin-I Converting Enzyme Activity in Serum, Clinical Chemistry, 1981, vol. 27, No. 11, pp. 1922-1925, see p. 3 of specification.
International Search Report dated Apr. 17, 2007.
Nishizawa, Mugio, et al.: "Efficient Syntheses of a Series of Trehalose Dimycolate (TDM)/Trehalose Dicorynomycolate (TDCM) Analogues and Their Interleukin-6 Level Enhancement Activity in Mice Sera," Journal of Organic Chemistry, 72(5), 1627-1633, 2007.
Supplementary European Search Report dated Feb. 10, 2009.

*Primary Examiner* — Elli Peselev
(74) *Attorney, Agent, or Firm* — Kratz, Quintos & Hanson, LLP

(57) ABSTRACT

The object of the present invention is to provide a novel trehalose compound having a high affinity for an adenosine A3 receptor. The trehalose compound of the present invention is represented by General Formula (1):

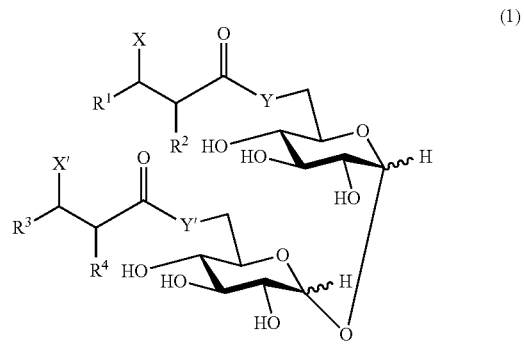

(1)

wherein X and X' represent a hydrogen atom, and the like; Y and Y' independently represent an oxygen atom, and the like; $R^1$ and $R^2$ independently represent a $C_1$-$C_6$ alkyl group; and $R^3$ and $R^4$ independently represent a $C_3$-$C_6$ alkyl group. The trehalose compound of the present invention has a remarkably high affinity for an adenosine A3 receptor.

11 Claims, No Drawings

TREHALOSE COMPOUND AND PHARMACEUTICAL COMPRISING THE COMPOUND

TECHNICAL FIELD

The present invention relates to a trehalose compound and a pharmaceutical comprising the trehalose compound.

BACKGROUND ART

Adenosine is widely distributed throughout the body, such as in the nervous system, and is involved, through adenosine receptors, in controlling various functions between cells. The adenosine receptors are classified into the subtypes of A1, A2 (2A and 2B), and A3. The tissue distribution and functions of the receptors are beginning to be identified.

Among these adenosine receptors, the human A3 receptor is distributed throughout tissues, such as lung, liver, placenta, brain, aorta, kidney, testicle, heart, etc. This receptor is activated by inflammation, hypoxia, ischemia, etc., of the aforesaid tissue. In light of the above, an adenosine A3 receptor antagonist is considered useful as an antiasthmatic drug, a therapeutic agent for chronic obstructive pulmonary disease, a brain protection medicine, antiphlogistic, etc.

As an adenosine A3 receptor antagonist, Patent Document 1 discloses a compound having the structure of pyrimidine; Patent Document 2 discloses a compound having the structure of adenine. As is seen in the disclosures of these publications, conventional adenosine A3 receptor antagonists have a common structure with the base of adenosine.

Heretofore, trehalose dimycolate (TDM) and trehalose dicorynomycolate (TDCM) are known as diesters of trehalose. TDM is identified as a glycolipid present on the cell surface of *Mycobacterium tuberculosis*, and is known to exhibit immune adjuvant activity and antitumor activity. TDCM, an analogue having a shorter carbon chain than that of TDM, is isolated from *Corynebacterium* spp. TDCM and its stereoisomer are found to respectively exhibit antitumor activity, and cancer metastasis inhibitory activity.

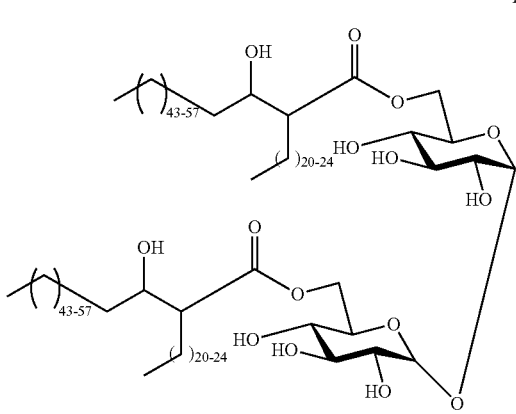

TDM

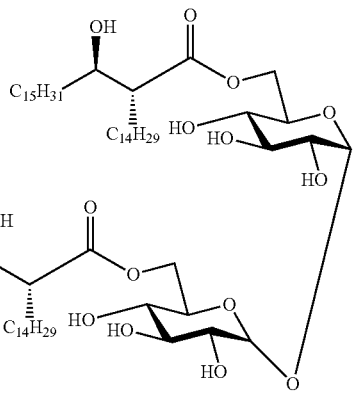

TDCM

Patent Document 3 discloses diesters of $C_7$-$C_{21}$ fatty acids and trehalose. However, the trehalose difatty acid esters are used therein as a surfactant. These esters are only mentioned as surfactants, along with trehalose monofatty acid esters, and alkylidene trehaloses, and with anionic surfactants, etc.; no specific examples of such diesters are disclosed in the publication.

Non-Patent Document 1 and Non-Patent Document 2 further disclose the trehalose diester compound shown below.

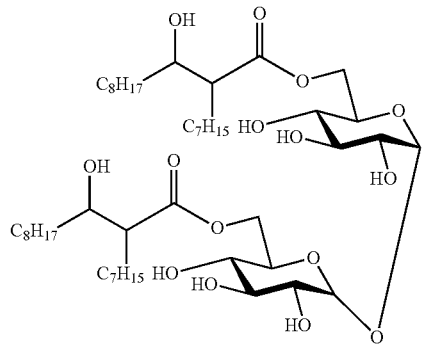

However, Non-Patent Document 1 merely discloses applying this compound as a measurement sample for FD-MS; Non-Patent Document 2 merely discloses examining the effect of the compound (glycolipid) on a phospholipid membrane.

Patent Documents 1: Japanese Unexamined Patent Publication No. H11-158073
Patent Documents 2: Japanese Unexamined Patent Publication No. 2003-519102
Patent Documents 3: Japanese Unexamined Patent Publication No. H11-171727 (Claim 6, and Examples)
Non-Patent Document 1: Jean-Claude Prome, Germain Puzo, Israel Journal of Chemistry, volume 17, pages 172-176, (1978)
Non-Patent Document 2: Y. Kasahara, Y. Ashihara, Clinical Chemistry, volume 27, No. 11, pages 1922-1925, (1981)

DISCLOSURE OF THE INVENTION

Problems to be Solved by the Invention

As described above, an adenosine A3 receptor antagonist has various physiological functions, and is expected to be used as a medicine; therefore, development of an antagonist having far higher affinity for adenosine A3 receptors is awaited.

An object of the present invention is to provide a novel compound having high affinity for adenosine A3 receptors.

Means for Solving the Problems

In order to solve the aforesaid problems, the present inventors conducted intensive research to develop a compound exhibiting excellent affinity for adenosine A3 receptors. Consequently, the inventors found that a newly synthesized diester of trehalose and a fatty acid having a relatively low carbon number exhibits distinctly superior antagonist activity against adenosine A3 receptors, compared with diesters of trehalose and a fatty acid having a relatively high carbon number. The present invention is accomplished based on such findings.

The present invention provides a trehalose compound and a pharmaceutical containing the trehalose compound according to Items 1 to 11.

Item 1. A trehalose compound represented by General Formula (I):

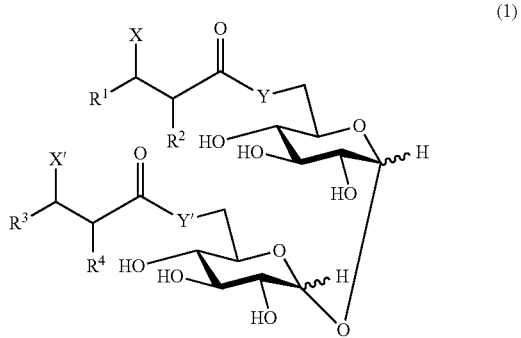

(1)

wherein X and X' are the same or different, and each represent a hydrogen atom, a hydroxy group, or a $C_1$-$C_6$ alkoxy group;

Y and Y' are the same or different, and each represent an oxygen atom or —$NR^5$— wherein $R^5$ represents a hydrogen atom or a $C_1$-$C_6$ alkyl group;

$R^1$ and $R^3$ each represent a $C_1$-$C_7$ alkyl group; and $R^2$ and $R^4$ each represent a $C_3$-$C_6$ alkyl group.

Item 2. The trehalose compound according to Item 1, wherein X and X' are both hydrogen atoms.

Item 3. The trehalose compound according to Item 1, wherein X and X' are both hydroxy groups.

Item 4. The trehalose compound according to Item 1, wherein X and X' are both methoxy groups.

Item 5. The trehalose compound according to any of Items 1 to 4, wherein Y and Y' are both oxygen atoms.

Item 6. The trehalose compound according to any of Items 1 to 4, wherein Y and Y' are both —NH—.

Item 7. The trehalose compound according to any of Items 1 to 6, wherein $R^1$ and $R^3$ are both n-hexyl groups.

Item 8. The trehalose compound according to any of Items 1 to 6, wherein $R^2$ and $R^4$ are both n-pentyl groups.

Item 9. The trehalose compound according to Item 1, which is selected from the group consisting of:

6,6'-bis-[(2-pentylnonanoylamino)]-6,6'-dideoxy-α,α'-trehalose;

6,6'-bis-[(2-pentylheptanoyl)]-α,α'-trehalose;

6,6'-bis-[(2R,3R)-3-methoxy-2-pentylnonanolyamino]-6,6'-dideoxy-α,α'-trehalose;

6,6'-bis-[(2R,3R)-3-methoxy-2-pentylnonanoylamino]-dideoxy-α,α'-trehalose;

6,6'-bis-[(2R,3S)-3-hydroxy-2-pentylnonanoyl]-α,α'-trehalose;

6,6'-bis-[(2R,3R)-3-hydroxy-2-pentylnonanoyl]-α,α'-trehalose; and 6,6'-bis-[(2S,3S)-3-hydroxy-2-pentylnonanoyl]-α,α'-trehalose.

Item 10. A pharmaceutical comprising the trehalose compound according to any of Items 1 to 9.

Item 11. An adenosine A3 receptor antagonist comprising the trehalose compound according to any of Items 1 to 9.

In the present invention, "$C_1$-$C_7$ alkyl group" refers to a $C_1$-$C_7$ straight- or branched-chain aliphatic hydrocarbon group, such as, for example, methyl, ethyl, n-propyl, isopropyl, n-butyl, isobutyl, tert-butyl, n-pentyl, isoamyl, n-hexyl, n-heptyl, and the like. $R^1$ or $R^2$ is preferably a $C_1$-$C_7$ straight-chain alkyl group, more preferably a $C_2$-$C_6$ straight-chain alkyl, still more preferably a $C_3$-$C_6$ straight-chain alkyl, and most preferably, n-hexyl.

"$C_1$-$C_6$ alkyl group" and "$C_3$-$C_6$ alkyl group" respectively refer to an alkyl group having a carbon number of 1 to 6 and 3 to 6 among the $C_1$-$C_7$ alkyl groups mentioned above. $R^3$ or $R^4$ is preferably a $C_3$-$C_6$ straight-chain alkyl group, more preferably a $C_4$-$C_6$ straight-chain alkyl group, and more preferably n-pentyl. $R^5$ preferably represents a $C_1$-$C_4$ alkyl group, more preferably a $C_1$-$C_2$ alkyl group, and still more preferably methyl.

"$C_1$-$C_6$ alkoxy group" refers to a $C_1$-$C_6$ straight- or branched-chain aliphatic hydrocarbon oxy group. Examples include methoxy, ethoxy, propoxy, isopropoxy, butoxy, isobutoxy, tert-butoxy, pentoxy, hexoxy, and the like. It is preferably a $C_1$-$C_4$ alkoxy, more preferably a $C_1$-$C_2$ alkoxy, and most preferably methoxy.

In the formula representing the trehalose compound of the present invention, X and X' are preferably both hydrogen atoms, hydroxy groups, or methoxy groups. Further, Y and Y' are preferably both oxygen atoms, or —NH—.

The compound represented by Formula (1) may contain one or more asymmetric centers, and may exist as enantiomers or diastereoisomers. The present invention encompasses mixtures thereof as well as separate individual isomers.

Trehalose has three types such as α,α'-trehalose, α,β'-trehalose, and β,β'-trehalose. As a trehalose compound of the present invention, α,α'-trehalose is preferred.

The compound represented by Formula (1) and a salt thereof may be present as solvates, which still falls within the scope of the present invention. Further, the compound represented by Formula (1) according to the invention encompasses a radioactively labeled form, which is useful for biology research.

Specific examples of the trehalose compounds of the present invention include the following compounds.

6,6'-bis-N-(2-pentylnonanoylamino)-6,6'-dideoxy-α,α'-trehalose 6,6'-bis-O-(2-pentylheptanoyl)-α,α'-trehalose 6,6'-bis-N-[(2R,3R)-3-methoxy-2-pentylnonanoylamino]-6,6'-dideoxy-α,α'-trehalose 6,6'-bis-O-[(2R,3R)-3-methoxy-2-pentylnonanoyl]-α,α'-trehalose 6,6'-bis-O-[(2R,3S)-3-hydroxy-2-pentylnonanoyl]-α,α'-trehalose 6,6'-bis-O-[(2R,3R)-3-hydroxy-2-pentylnonanoyl]-α,α'-trehalose 6,6'-bis-O-[(2S,3S)-3-hydroxy-2-pentylnonanoyl]-α,α'-trehalose 6-O-[(2R,3R)-3-hydroxy-2-pentylnonanoyl]-6'-O-[(2S,3S)-3-hydroxy-2-pentylnonanoyl]-α,α'-trehalose 6,6'-bis-O-[(2R,3R)-2-hexyl-3-hydroxydecanoyl]-α,α'-trehalose 6,6'-bis-O-[(2S,3S)-2-hexyl-3-hydroxydecanoyl]-α,α'-trehalose 6-O-[(2R,3R)-3-hydroxy-2-hexyldecanoyl]-6'-O-[(2S,3S)-3-hydroxy-2-hexyldecanoyl]-α,α'-trehalose 6,6'-bis-O-[(2S,3R)-3-hydroxy-2-pentylnonanoyl]-α,α'-trehalose 6,6'-bis-N-[(2R,3R)-3-hydroxy-2-pentylnonanoylamino]-6,6'-dideoxy-α,α'-trehalose 6,6'-bis-O-(2-butylhexanoyl)-α,α'-trehalose 6,6'-bis-O-(2-hexyloctanoyl)-α,α'-trehalose 6,6'-bis-O-(2-pentylnonanoyl)-α,α'-trehalose 6-O-[(2R,3R)-2-butyl-3-hydroxyoctanoyl]-6'-O-[(2S,3S)-2-butyl-3-hydroxyoctanoyl]-α,α'-trehalose 6,6'-bis-N-(2-hexyloctanoylamino)-6,6'-dideoxy-α,α'-trehalose Preferable examples of the trehalose compounds of the present invention include the following compounds.

6,6'-bis-N-(2-pentylnonanoylamino)-6,6'-dideoxy-α,α'-trehalose 6,6'-bis-O-(2-pentylheptanoyl)-α,α'-trehalose 6,6'-bis-N-[(2R,3R)-3-methoxy-2-pentylnonanoylamino]-6,6'-dideoxy-α,α'-trehalose 6,6'-bis-O-[(2R,3R)-3-methoxy-2-pentylnonanoyl]-α,α'-trehalose 6,6'-bis-O-[(2R,3S)-3-hydroxy-2-pentylnonanoyl]-α,α'-trehalose 6,6'-bis-O-[(2R,3R)-3-hydroxy-2-pentylnonanoyl]-α,α'-trehalose 6,6'-bis-O-[(2S,3S)-3-hydroxy-2-pentylnonanoyl]-α,α'-trehalose 6-O-[(2R,3R)-3-hydroxy-2-pentylnonanoyl]-6'-O-[(2S,3S)-3-hydroxy-2-pentylnonanoyl]-α,α'-trehalose 6,6'-bis-O-[(2S,3R)-3-hydroxy-2-pentylnonanoyl]-α,α'-trehalose A pharmaceutical and an adenosine A3 receptor antagonist of the present invention contain the trehalose compound mentioned above.

The trehalose compound of the present invention represented by General Formula (1) (hereinafter sometimes referred to as "Trehalose Compound (1)") can be produced according to, for example, the following Synthetic Scheme 1.

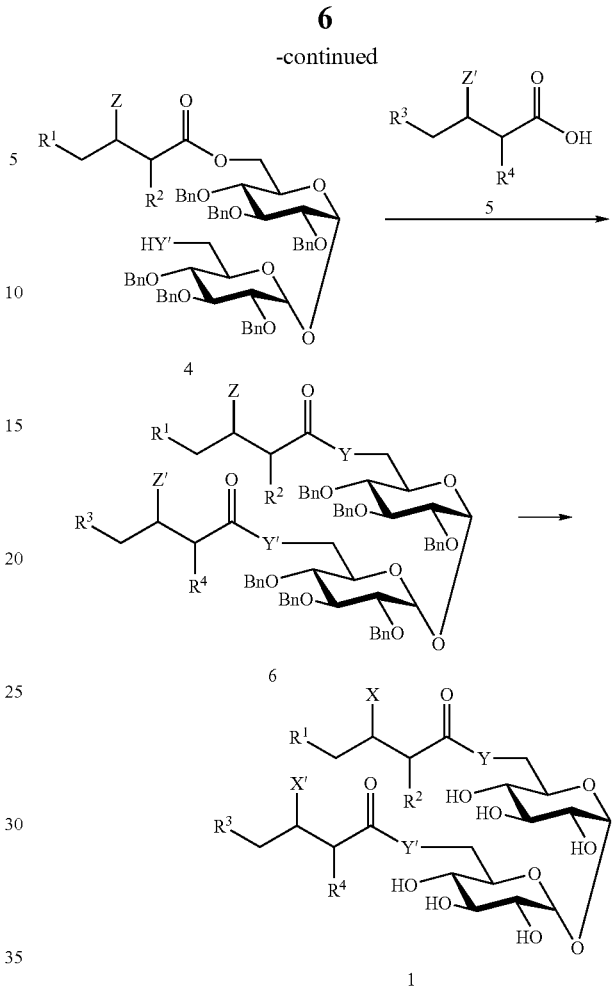

In the synthetic scheme above, Y, Y', and $R^1$-$R^4$ have the same meaning as defined above. Bn represents a benzyl group. Z and Z' represent either a hydrogen atom, a $C_1$-$C_6$ alkoxy group, which are included in the definitions of X and X', or a —OBn group. The scheme above only shows Trehalose Compound 2, etc., being α,α'-trehalose; however, α,β'-, and β,β'-trehalose may also be synthesized in the same manner.

Synthetic Scheme 1 is a process for producing Trehalose Compound (1) by an esterification reaction or an amidation reaction of Trehalose Compound 2, and Carboxylic Acid Compounds 3 and 5.

Among Trehalose Compounds 2 used as a starting material, the one in which Y and Y' are both oxygen atoms may be any of those commercially available, or synthesized from a trehalose, etc., according to a known method. For example, α,α'-trehalose can be easily obtained as it naturally occurs. α,β'- and β,β'-trehalose may be obtained by respectively reacting, in a solvent, a mixture of α- or β-D-glucopyranose and α-D-glucopyranosyl chloride, in which the hydroxy groups at the 2, 3, 4, and 6 positions are protected, in the presence of AgOTf and a molecular sieve 4A (see, M. Nishizawa et al., Chem. Pharm. Bull., volume 42 (4), pages 982-984, 1994). With regard to trehalose, the hydroxy group at the 6 position and other hydroxy groups have different reactivities; therefore, Trehalose Compound 2 in which Y and Y' are both oxygen atoms, can relatively readily be synthesized. A trehalose compound in which Y and Y' are both —$NR^5$—, and a trehalose compound in which one of Y and Y' is an oxygen atom and the other is —NR⁵—, may be synthesized according to a process disclosed in the document (Wang J. et al., Bioorganic Medicinal Chemistry, volume 12, pages 6397-6413, 2004), or to a similar process thereto. Usable Carboxylic Acid Compounds 3 and 5 employed herein may be any of those commercially available, or synthesized according to Synthetic Schemes 2 to 4 described later.

In the first step of Synthetic Scheme 1 (hereinafter, each step of the schemes is referred sequentially to as "Step 1", etc.), Trehalose Compound 4 is obtained by an esterification reaction or an amidation reaction of Trehalose Compound 2 and Carboxylic Acid Compound 3. Then, Trehalose Compound 6 is obtained by an esterification reaction or an amidation reaction of Trehalose Compound 4 and Carboxylic Acid Compound 5.

Any general reaction method may be applied to such an esterification and amidation reaction, such as, for example, dehydrating methods (including a carbodiimide method), mixed acid anhydride methods, activated ester methods, and the like. In these methods, usable dehydrating agents may be any agent that is usually used in an ester synthesis or amide synthesis from an alcohol or an amine, and a carboxylic acid. Examples include mineral acids, such as hydrogen chloride, sulfuric acid, hydrochloric acid, etc.; organic acids, such as para-toluenesulfonic acid, camphorsulfonic acid, etc.; lewis acids, such as boron fluoride etherate, etc., and carbodiimides. The reaction conditions of the carbodiimide method, which is one of the dehydrating methods, for example, involve using, as a dehydrating agent, carbodiimides, such as dicyclohexylcarbodiimide, 1-ethyl-3-(3-dimethylaminopropyl) carbodiimide hydrochloride, etc.; and adding a catalyst, such as dimethylaminopyridine, 4-pyrrolidinopyridine, etc. In order to facilitate the reaction, devices, such as a Dean-Stark water separator, which uses, as a solvent, benzene, toluene, etc.; a Soxhlet extractor containing a desiccant, etc., may be used. Examples of usable desiccants include anhydrous magnesium sulfate, molecular sieves (4A, 5A), etc. The proportions of starting material compound, dehydrating agent, and catalyst are not limited, and can be suitably selected from a wide range.

The aforesaid esterification reaction or amidation reaction is usually carried out in a suitable solvent. Usable solvents are not limited as long as the solvent exhibits moderate solubility of a starting material compound, and is inactive having no adverse effects during the reaction. Examples of such solvents include halogenated hydrocarbons, such as methylene chloride, chloroform, ethane dichloride, etc.; ethers, such as tetrahydrofuran, diethyl ether, monoglyme, etc.; and aromatic hydrocarbons, such as toluene, xylene, etc.

The reaction temperature of the esterification or amidation is not limited, but is usually from 0° C. to 200° C., and preferably from room temperature to 100° C. The reaction time is usually from 1 hour to 1 week, and preferably from 1 to 24 hours.

After the reaction is completed, the mixed reaction solution was subjected to general treatments such as separation and removal of the by-product, drying of the product, distilling of the solvent, etc., and then to purification according to a general method, such as silica gel column chromatography.

In the reaction of Step 1, the HY-group at the 6 position of either of the glucoses in Trehalose Compounds 4 can be esterified, etc. Therefore, desired Trehalose Compound 4 in which HY-group at the 6 position was esterified is recovered and purified after the reaction. Alternatively, in order to improve the reaction yield, a HY'-group at the 6 position of Trehalose Compound 2 used as a starting material, not desired to be esterified with Carboxylic Acid Compound 3, may be selectively protected before the reaction is carried out. Then, when the esterification reaction or amidation reaction is completed, such a HY'-group may be selectively deprotected.

Next in Step 2, the HY'-group of Trehalose Compound 2 that was not esterified in Step 1 is esterified or amidated with Carboxylic Acid Compound 5 in the same manner as Step 1 above.

When the objective compound is Trehalose Compound 1 in which both carboxylic acid portions are identical, two steps of esterification reaction, etc., in Synthetic Scheme 1 may be carried out in a single step. Specifically, use of an amount of about 1 mol of Carboxylic Acid Compound 3 per mol of Trehalose Compound 2 allows to produce, as a main product, a monoester or a monoamide, while use of an amount of 2 mol or more of the carboxylic acid compound allows to produce, as a main product, diesters, etc., in which two of the hydroxy groups at the 6 position are esterified by an identical carboxylic acid compound.

Subsequently, Trehalose Compound 6 obtained in Steps 1 and 2 is subjected to a catalytic hydrogenation reaction in a hydrogen atmosphere to produce Trehalose Compound (1) of the present invention. Usable catalysts may be any of those conventionally employed in a contact hydrogenation reaction, such as, for example, platinum oxide, platinum carbon, palladium hydroxide, palladium carbon, Raney nickel, etc. The amount thereof is generally from 0.1 to 50 mass % based on the substrate, and hydrogen pressure is usually from 1 to 100 atmospheres, and preferably 1 to 3 atmospheres.

Such a reaction is usually carried out in a suitable solvent. Usable solvents include any inactive solvents having no adverse effects during the reaction. Examples include alcohols, such as methanol, ethanol, etc.; esters, such as ethyl acetate, methyl acetate, etc.; and halogenated hydrocarbons, such as dichloromethane, chloroform, dichloroethane, etc. Although the reaction temperature is not limited, it is usually from 0° C. to 100° C., and preferably from room temperature to 50° C. The reaction time is usually from 1 to 50 hours, and preferably from 1 to 30 hours.

After the reactions of each step, the resulting solution is subjected to general treatments, such as separation of the catalyst by filtration, distillation of the solvent, etc., and then to purification according to a general method, such as solvent extractions, silica gel column chromatography, etc.

Carboxylic Acid Compound 3, used as a starting material compound in Synthetic Scheme 1, can be produced according to, for example, the following Synthetic Schemes 2 to 4. In Synthetic Schemes 2 to 4, Carboxylic Acid Compound 3 is described as an objective compound. Carboxylic Acid Compound 5, which is also used as a starting material compound, can be produced in the same manner as for Carboxylic Acid Compound 3.

Among the Carboxylic Acid Compounds 3 used as a starting material in Synthetic Scheme 1, Carboxylic Acid Compounds 3a and 3b used for obtaining a compound in which the X group is finally a hydroxy group, may be synthesized according to, for example, Synthetic Scheme 2 below.

Synthetic Scheme 2

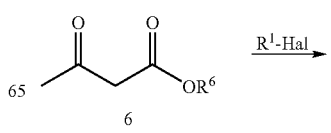

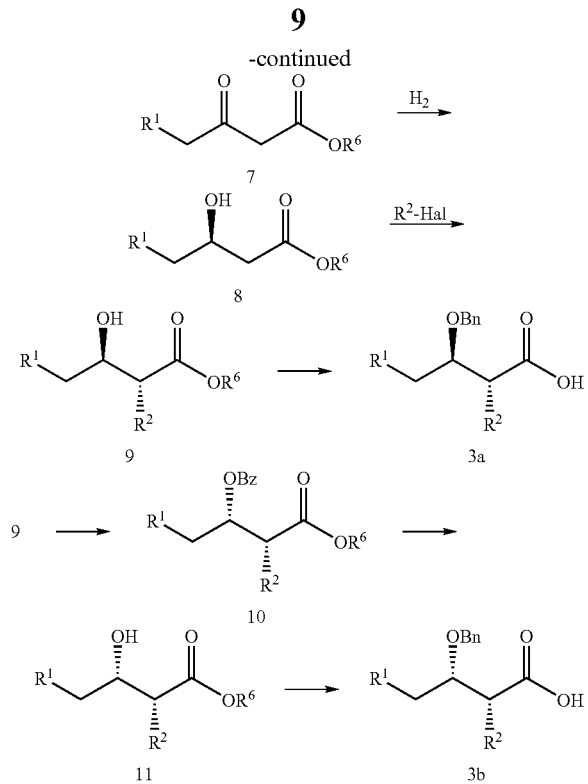

In the synthetic scheme above, $R^1$, $R^2$, and Bn have the same meanings as defined above. $R^6$ represents a $C_1$-$C_6$ alkyl group; Hal represents a halogen atom, such as a chlorine atom, bromine atom, iodine atom, etc.; Bz represents a benzoyl group; Z and Z' represent either of a hydrogen atom, a $C_1$-$C_6$ alkoxy group, which are both included in the definitions of X and X', or a —OBn group. The scheme above only shows (R)-Compound 8; however, (S)-compound may also be synthesized as explained below. Therefore, four optical isomers at the 2 and 3 positions may be synthesized in Synthetic Scheme 2 above.

Synthetic Scheme 2 is a process for producing carboxylic acid compound in which the Z group is a —OBn group. The produced carboxylic acid compound is used as Carboxylic Acid Compound 3 or 5, which are used as starting materials in Synthetic Scheme 1, to produce Trehalose Compound (1) in which the X group is finally a hydroxy group.

Usable Acetoacetic Ester 6 employed as a starting material may be, as it has a relatively simple structure, any of those commercially available, or synthesized according to a known method.

Step 1 of Synthetic Scheme 2 is a process for synthesizing Compound 7 by subjecting Acetoacetic Ester 6 to an alkyl halide reaction in the presence of a basic compound. The reaction is advantageously conducted in the presence of metal iodides, such as sodium iodide, potassium iodide, etc. Preferable examples of $R^6$, which is a protecting group for carboxyl groups, include methyl, ethyl, isopropyl, t-butyl group, etc.

Any known basic compounds are usable. Preferred are sodium hydride, potassium hydride, n-butyl lithium, and like strong bases. These may be used in combination.

The proportion of Acetoacetic Ester 6 and alkyl halide is not limited, and is suitably selected from a wide range. It is, however, usually from 1 to 5 mol, and preferably 1 to 1.5 mol of alkyl halide per mol of Acetoacetic Ester 6. Further, the proportion of Acetoacetic Ester 6 and a basic compound is not limited and is suitably selected from a wide range. It is, however, usually from 1 to 1.5 mol, and preferably from 2 to 3 mol of the basic compound per mol of Acetoacetic Ester 6.

The reaction in Step 1 is usually carried out in a suitable solvent. Usable solvents include any inactive solvents having no adverse effects during the reaction. Examples include ethers, such as tetrahydrofuran, diethyl ether, monoglyme, etc.; and aromatic hydrocarbons, such as toluene and xylene, etc. Although the reaction temperature is not limited, it is usually from −20° C. to 100° C., and preferably from −10° C. to room temperature. The reaction time is usually from 30 minutes to 30 hours, and preferably from 1 to 10 hours.

In the next Step 2, Compound 7 is reduced by adding a small amount of a base, such as triethylamine, etc., to synthesize Compound 8.

Optically active Compound 8 is produced according to an asymmetric hydrogenation reaction using an asymmetric ligand or a complex thereof as a catalyst. Usable asymmetric ligands or complexes thereof may be any of those as long as they are used in an asymmetric hydrogenation reaction. Examples include a 2,2'-bis(diphenylphosphino)-1,1'-binaphthyl (BINAP) based complex (e.g. an optically active BINAP-ruthenium complex); diamine complexes, such as optically active 1,2-dianilinoethane-ruthenium complexes, etc.; bis(oxazolynyl)pyridine-rhodium complexes, etc. Among these catalysts, the use of (R) dichloro(2,2'-bis(diphenylphosphino)-1,1'-binaphthyl) ruthenium (hereinafter referred to as "BINAP-Ru") for reduction facilitates the production of (R)-Compound 8 in a high optical yield; use of (S)-BINAP-Ru facilitates the production of (S)-Compound 8 in a high optical yield. The amount used is a catalytic amount, and the proportion is usually from 0.0001 to 0.5 mol, and preferably from 0.001 to 0.01 moil per mol of Compound 7.

The reaction in Step 2 is usually carried out in a suitable solvent. Usable solvents may be any of those having no adverse effects during the reaction. Examples include methanol, ethanol, isopropanol, and like alcohols; tetrahydrofuran, diethyl ether, monoglyme, and like ethers.

Although the reaction temperature is not limited, it is usually from 0° C. to 200° C., and preferably from 0° C. to 50° C. The reaction time is usually from 1 hour to 5 days, and preferably from 1 hour to 30 hours.

The reaction is carried out in a hydrogen atmosphere using a pressure-resistant container. The hydrogen pressure is usually from 1 to 200 atmospheres, and preferably from 2 to 100 atmospheres.

Next in Step 3, Compound 8 is alkylated with an alkyl halide in the presence of a basic compound to produce Compound 9. The reaction is advantageously carried out in the presence of metal iodides, such as sodium iodide, potassium iodide, etc. Preferable examples of the basic compound include sodium hydride, potassium hydride, n-butyl lithium, LDA (lithium diisopropylamide), and like strong bases. These may be used in combination.

The product produced in the reaction mainly has an anti-conformation of the hydroxy group of Compound 9 and newly introduced alkyl group. Specifically, (R)-Compound 8 produces (RR)-Compound 9, and (S)-Compound 8 produces (SS)-Compound 9 respectively with a high diastereoselectivity of 97% or more.

The proportion of Compound 8 and an alkyl halide is not limited, and may be suitably selected from a wide range. An alkyl halide is usually employed in a proportion of 1 to 5 mol, and preferably 1 to 2 mol per mol of Compound 8. The proportion of Compound 8 and a basic compound is not limited, and may be suitably selected from a wide range. It is, however, usually from 1 to 10 mol, and preferably from 2 to 4 mol of the basic compound per mol of Compound 8.

Such a reaction is usually carried out in a suitable solvent. Usable solvents include any inactive solvents having no adverse effects during the reaction. Examples include tetrahydrofuran, diethyl ether, monoglyme, and like ethers; and toluene, xylene, and like aromatic hydrocarbons. Although the reaction temperature of such a reaction is not limited, it is usually from −78° C. to 50° C., and preferably from −78° C. to room temperature. The reaction time is usually from 1 to 30 hours, and preferably from 30 minutes to 5 hours.

Next in Step 4, Compound 9 is subjected to a reductive etherification reaction, and then the resulting product is subjected to hydrolysis so as to synthesize Carboxylic Acid Compound 3a. Specifically, Compound 9 is first treated with trimethylchlorosilane in the presence of a basic compound to give silyl ether. Then, benzaldehyde and triethylsilane are added to the obtained silyl ether, which is subjected to a reductive etherification reaction at a low temperature in the presence of trimethylsilyl triflate as a catalyst to produce a compound having a benzylated hydroxy group. Further, when $R^6$ is a t-butyl group, an increase, after the reaction, of the temperature of the reaction mixture to room temperature allows the t-butyl group to be released, making it possible to produce the objective Compound 3a in one pot.

In the silylation reaction as the first process of the reaction, usable trimethylsilylation agent may be any of those usually employed in a trimethylsilylation reaction. Examples include chlorotrimethyl silane and like trimethylsilane halides; hexamethyldisilazanes; and bis(trimethylsilyl)urea, etc. The proportion of Compound 9 and a silylation agent is not limited, and may be selected from a wide range. The silylation agent is usually used in a proportion of 1 to 5 mol, preferably 1 to 2 mol per mol of Compound 9.

Examples of a usable basic compound herein include any inorganic compounds or organic compounds that are used in a usual silylation reaction. Preferable examples are organic amines, such as triethylamine, pyridine, etc. The proportion of Compound 9 and a basic compound is not limited, and may be selected from a wide range. The basic compound is usually used in a proportion of 1 to 10 mol, preferably 1 to 2 mol per mol of Compound 9.

Further, Step 4 is performed in the presence of catalyst. A preferable catalyst is trimethylsilyl triflate. The amount used is a catalytic amount. Specifically, it is from 0.01 to 0.8 mol per mol of Compound 9.

In the reductive etherification reaction as the second step of the reaction, the proportion of benzaldehyde, triethylsilane, and Compound 9 is not limited, and may be selected from a wide range. Triethylsilane and a reagent of Compound 9 each are used usually in a proportion of 1 to 10 mol, and preferably 1 to 2 mol per mol of benzaldehyde.

Such a reaction is usually carried out in a suitable solvent. Usable solvents include any inactive solvents having no adverse effects during the reaction. Examples include ethers, such as tetrahydrofuran, diethyl ether, monoglyme, etc.; halogenated hydrocarbons, such as methylene chloride, chloroform, ethanedichloride, etc.; aromatic hydrocarbons, such as toluene, xylene, etc.; acetonitriles; and DMF, etc.

Although the reaction temperature in this step is not limited, it is usually from −20° C. to 100° C., and preferably from 0° C. to 50° C. The reaction time is usually from 5 minutes to 24 hours, and preferably from 30 minutes to 10 hours. Further, although the reaction temperature in the process is not limited, it is usually from −80° C. to 50° C., and preferably from −80° C. to 0° C. The reaction time is usually from 5 minutes to 24 hours, and preferably from 30 minutes to 10 hours.

In Step 5, Compound 10, having a hydroxy group that is sterically inverted, may be synthesized. Specifically, Compound 8 is subjected to a Mitsunobu reaction with dialkyl azodicarboxylate, triphenylphosphine and benzoic acid.

Examples of usable dialkyl azodicarboxylate include diethyl azodicarboxylate, diisopropyl azodicarboxylate, etc. The proportions of dialkyl azodicarboxylate, triphenylphosphine, and benzoic acid per mol of Compound 9 are not limited, and may be suitably selected from a wide range. Usually, dialkyl azodicarboxylate, triphenylphosphine, and benzoic acid each are used in a proportion of 1 to 3 mol, preferably 1 to 1.5 mol per mol of Compound 9.

Such a reaction is usually conducted in a suitable solvent. Usable solvents are any of those conventionally used in the Mitsunobu reaction. Examples include aromatic hydrocarbons, such as toluene, chlorobenzene, etc.

The reaction temperature is usually from −50 to 50° C., and preferably −30° C. to room temperature. The reaction time is usually 10 minutes to 10 hours, and preferably 30 minutes to 3 hours.

In Step 6, the —OBz group of Compound 10 is deprotected to synthesize Compound 11. Specifically, hydrolysis using an alkyl tin reagent is carried out according to a method, such as Salomon, etc. (Salomon, C. J.; Mata, E. G.; Mascaretti, O. A., J. Org. Chem., 1994, volume 59, pages 7259-7266).

Examples of usable alkyl tin reagent include bistributyltin oxide, bis triethyltin oxide, etc. The proportion of such a tin reagent is usually from 1.5 to 2 mol, and preferably about 1.2 mol per mol of Compound 10.

Such a reaction is usually carried out in a solvent. Any conventional solvents may be used therefor, such as, for example, aromatic hydrocarbons, such as toluene, chlorobenzene, etc. The reaction temperature is usually from 100° C. to 130° C., and preferably from 100° C. to 120° C. The reaction time is usually from 10 to 50 hours, and preferably from 10 to 20 hours.

After the reactions are completed in each step, the objective compounds are recovered and purified according to known procedures, such as silica gel column chromatography, vacuum distillation, etc.

Next in Step 7, the objective Carboxylic Acid Compound 3b is produced from Compound 11 under the same conditions as those applied for producing Carboxylic Acid Compound 3a from Compound 9.

Among Carboxylic Acid Compounds 3 used as a starting material in Synthetic Scheme 1, Carboxylic Acid Compound 3c in which the Z group is a $C_1$-$C_6$ alkoxy group may be produced according to, for example, the following Synthetic Scheme 3.

Synthetic Scheme 3

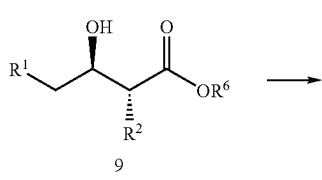

9

-continued

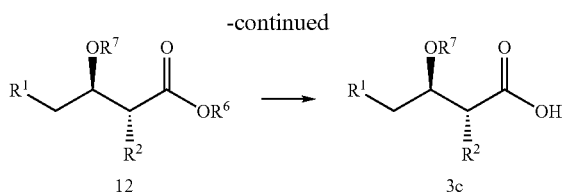

12  3c

In the synthetic scheme above, $R^1$, $R^2$, and $R^6$ have the same meaning as defined above. $R^7$ represents a $C_1$-$C_6$ alkyl group. Although (2R,3R)-compound is only shown as Compound 9 in the scheme above, (2S,3S)-compounds may also be synthesized as explained in Scheme 2. Further, the conformations at the 3 position of Compounds 9 and 12 sterically maintained may be inverted as described later. Accordingly, four optical isomers as Carboxylic Acid Compounds 3c can be produced in Synthetic Scheme 3.

Synthetic Scheme 3 is a process for producing a carboxylic acid compound utilizing, as a starting material, Compound 9 used in Synthetic Scheme 2. The produced carboxylic acid compound is used as Carboxylic Acid Compounds 3 or 5, which are starting materials in Synthetic Scheme 1, to produce Trehalose Compound (1) in which the X group is finally a $C_1$-$C_6$ alkoxy group.

Step 1 of Synthetic Scheme 3 involves etherification of a hydroxy group of Compound 9. In this step, an alkyl etherification reaction, which is carried out using an alkyl sulfonate in the presence of a basic compound, may be utilized. Use of the aforementioned reagents retains the steric conformation at the 3 position. Examples of usable alkyl sulfonates include alkyl esters of trifluoromethane sulfonic acid, alkyl esters of p-toluenesulfonic acid, etc. Examples of usable methyl etherification reagents include methyl trifluoromethanesulfonate, methyl p-toluenesulfonate, etc. The proportion of Compound 9 and the alkyl sulfonate is not limited, and may be selected from a wide range. Alkyl sulfonate is usually used in a proportion of 1 to 5 mol, and preferably 1 to 1.5 mol per mol of Compound 9.

Usable basic compounds may be any of an inorganic compound or an organic compound. Preferred are organic bases, such as 2,6-t-butylpyridine, 4-dimethylaminopyridine, etc. The proportion of Compound 9 and the basic compound is not limited, and is suitably adjusted. It is, however, usually in a proportion of 1 to 5 mol, and preferably 1 to 2 mol of basic compound per mol of Compound 9.

Such a reaction is carried out in a suitable solvent. Usable solvents may be any inactive solvents having no adverse effects during the reaction. Examples include halogenated hydrocarbons, such as methylene chloride, chloroform, ethane dichloride, etc.; ethers, such as tetrahydrofuran chloride, diethyl ether, etc.; aromatic hydrocarbons, such as toluene, xylene, etc.

Although the reaction temperature is not limited, it is usually from –20° C. to 100° C., and preferably from room temperature to 50° C. The reaction time is usually from 1 hour to 2 days, and preferably from 1 hour to 30 hours.

Apart from the alkyl etherification reaction above, when inverting the steric conformation at the 3 position, a hydroxy group may be p-toluenesulfonylated, etc., to form a leaving group, and then an $S_N2$ reaction using a desired $C_1$-$C_6$ alkoxide may be carried out. Any known conditions for an $S_N2$ reaction may be applied to the reaction.

If Compound 12 obtained in Step 1 above is a compound in which $R^6$ is t-$C_4H_9$ or prenyl, Carboxylic acid 3c may be produced by decomposing an ester group using trimethylsilyl triflate as a catalyst. In this reaction, the proportion of Compound 12 and trimethylsilyl triflate is not limited, and may be selected from a wide range. Trimethylsilyl triflate herein is usually used in a proportion of 0.05 to 2 mol, and preferably 0.1 to 0.7 mol per mol of Compound 12.

Such a reaction is carried out in a suitable solvent. Usable solvents include any inactive solvents having no adverse effects during the reaction. Examples include halogenated hydrocarbons, such as methylene chloride, chloroform, ethane dichloride, etc.; ethers, such as tetrahydrofuran chloride, diethyl ether, etc.; and aromatic hydrocarbons, such as toluene, xylene, etc. Although the reaction temperature is not limited, it is usually from –20° C. to 200° C., and preferably from room temperature to 50° C. The reaction time is usually 1 hour to 2 days, and preferably 1 hour to 30 hours.

After the reactions are completed in each step, the objective compounds are recovered and purified according to known processes, such as silica gel column chromatography, vacuum distillation, etc.

Among Carboxylic Acid Compounds 3 used as a starting material in Synthetic Scheme 1, Carboxylic Acid Compound 3d in which the Z group is a hydrogen atom may be synthesized according to, for example, Synthetic Scheme 4 below. As necessary, Creger, J. Am. Chem. Soc., volume 92, pages 1397-98, 1970, may be referred to.

Synthetic Scheme 4

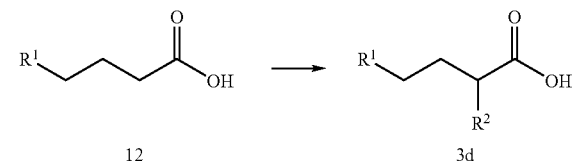

12  3d

In the synthetic scheme above, $R^1$ and $R^2$ have the same meaning as defined above.

Synthetic Scheme 4 is a process for obtaining Carboxylic Acid Compound 3d by subjecting Compound 12 to a general alkylation reaction. Compound 12 used as a starting material herein may be any of those commercially available.

The alkylation reaction may be carried out in accordance with any known process. Examples include the method disclosed in Creger, J. Am. Chem. Soc., 92, pages 1397-1398, 1970. More specifically, a strong base is added to a solution of Compound 12, abstracting a hydrogen atom at the 2 position therefrom, and subjecting the resulting solution to a reaction with the corresponding alkyl halide.

Examples of usable solvents include ethers, such as diethyl ether, tetrahydrofuran, etc. Examples of usable strong bases include sodium hydride, etc. Additionally, lithium diisopropylamide may be utilized in combination to carry out an exchange reaction between protons and lithium. Although the proportion of Compound 12 and the strong base may be selected from a wide range, the strong base is usually used in a proportion of 0.9 to 1.2 mol per mol of Compound 12. The heating temperature therefor is usually about –80° C. to about 60° C., and preferably about room temperature to about 60° C. The reaction time is about 30 minutes to about 6 hours.

Subsequently, an alkyl halide is added to the reaction mixed solution. Although the proportion of Compound 12 and the alkyl halide may be selected from a wide range, it is usually used in a proportion of about 1.1 to about 2 mol of alkyl halide per mol of Compound 12. The reaction temperature herein may be set to about room temperature. The reaction time is usually about 2 hours to about 12 hours.

After the reaction is completed, the objective compound is recovered and purified according to known processes, such as silica gel column chromatography, vacuum distillation, etc.

Trehalose Compound (1) of the present invention exhibits excellent adenosine A3 receptor selectivity as well as high affinity therefor. Trehalose Compound (1) is therefore expected to be used as, while serving as an adenosine A3 receptor antagonist, a prophylactic or therapeutic agent for diseases caused by the binding of adenosine to an adenosine A3 receptor.

Trehalose Compound (1) of the present invention is administered as it is or as a pharmaceutical preparation to a human or an animal. Such pharmaceutical preparations are obtained by formulating the compound of the present invention into pharmaceutical preparations, using usually employed diluents or excipients such as fillers, extenders, binders, wetting agents, disintegrants, surfactants, lubricants, etc. The form of such pharmaceutical preparations can be selected from various forms according to the purpose of therapy. Typical examples include tablets, pills, powders, solutions, suspensions, emulsions, granules, capsules, suppositories, injections (solutions, suspensions, emulsions, etc.) and the like. Such pharmaceutical preparations may be produced in accordance with a usual method.

The dosage of the pharmaceutical preparation above is suitably selected according to the usage, patient's age, gender, severity of disease, and other conditions. Trehalose Compound (1) as an active ingredient is usually administered in an amount of 0.01 to 100 mg, and preferably 0.1 to 50 mg/kg body weight per day, in single or divided doses.

As the dosage varies depending on various conditions, a dosage smaller than the above range may be sufficient; or a dosage larger than the above range may be required.

Hereinafter, the present invention is explained in more detail with reference to the Examples. However, the present invention is not limited thereto, and any suitable modification may be made without departing from the spirit and scope of the invention. Such modifications are encompassed in the technical scope of the present invention.

Effect of the Invention

The Trehalose compound of the present invention is an adenosine A3 receptor antagonist exhibiting high affinity for an adenosine A3 receptor. The trehalose compound of the present invention is, therefore, usable as a prophylaxis and/or treating agent for diseases related to adenosine A3 receptors, such as asthma, chronic obstructive pulmonary diseases, cerebropathy, inflammations, and the like.

BEST MODE FOR CARRYING OUT THE INVENTION

Production Example A-1

Production of 3-oxooctanoic acid t-butyl ester

Anhydrous THF (200 ml) was introduced into a dried two-necked flask to which sodium hydride (60 w/w %, 2.71 g, 67.8 mmol) was added. The temperature thereof was allowed to fall to 0° C., and t-butyl acetoacetate (9.00 g, 56.9 mmol) was added dropwise thereto. The resulting mixture was stirred for 10 minutes while maintaining the temperature thereof at 0° C., and then n-butyllithium (1.6M hexane solution, 39.1 ml, 62.6 mmol) was added dropwise. After the obtained mixture was stirred for 30 minutes at 0° C., 1-iodobutane (13.6 g, 73.9 mmol) was added thereto, and then stirred for 6 hours. A saturated ammonium chloride solution was added to the obtained mixture and extracted 3 times with diethyl ether. The resulting organic layer was dried with anhydrous magnesium sulfate, filtered and concentrated. The obtained residue was purified by column chromatography (silica gel: 200 g, n-hexane/ethyl acetate=10/1) to produce the target compound (11.3 g, 73%).

FT-IR (neat): 2979, 2873, 1748 cm$^{-1}$ $^1$H-NMR (300 MHz, CDCl$_3$) $\delta$0.89 (3H, t, J=6.9 Hz), 1.29 (4H, m), 1.47 (9H, s), 1.58 (2H, m), 2.52 (2H, t, J=7.4 Hz), 3.33 (2H, s)

$^{13}$C-NMR (75 MHz, CDCl$_3$) $\delta$13.6, 22.2, 22.9, 27.7, 28.1, 31.0, 42.6, 50.4, 81.4, 166.3, 203.1

EIMS m/z (%) 215 (7 M$^+$+1), 199 (10), 159 (100), 89 (18)

HRMS (CI$^+$) m/z Calculation Value: C$_{12}$H$_{23}$O$_3$(M$^+$+1) 215.1647, Actual Measurement Value: 215.1644

Production Example A-2

Production of 3-oxo-nonanoic acid t-butyl ester

The target compound (10.8 g, 66%) was obtained in the same manner as in Production Example A-1, except that 1-iodopentane (14.6 g, 73.7 mmol) was used.

FT-IR (neat) 2958, 2932, 2860, 1740, 1715 cm$^{-1}$ $^1$H-NMR (300 MHz in CDCl$_3$) $\delta$0.88 (3H, t, J=6.9 Hz), 1.28 (6H, m), 1.47 (9H, s), 1.59 (2H, m), 2.52 (2H, t, J=7.6 Hz), 3.34 (2H, s)

$^{13}$C-NMR (75 MHz in CDCl$_3$) $\delta$14.0, 22.4, 23.4, 27.9, 28.7, 31.5, 42.9, 50.6, 81.8, 166.5, 203.5

CIMS m/z (%) 229 (54 M$^+$+1), 213 (70), 174 (92), 173 (100), 172 (85), 155 (52), 113 (92), 102 (55)

HRMS (CI$^+$) m/z Calculation Value: C$_{13}$H$_{25}$O$_3$(M$^+$+1) 229.1804, Actual Measurement Value: 229.1810

Production Example A-3

Production of 3-oxodecanoic acid t-butyl ester

The target compound (9.10 g, 96%) was obtained in the same manner as in Production Example A-1, except that 1-iodohexane (12.4 g, 58.5 mmol) was used.

FT-IR (neat) 2955, 2929, 2857, 1735, 1714 cm$^{-1}$ $^1$H-NMR (300 MHz in CDCl$_3$) $\delta$0.88 (3H, t, J=7.1 Hz), 1.28 (8H, m), 1.47 (9H, s), 1.59 (2H, m), 2.52 (2H, t, J=7.4 Hz), 3.34 (2H, s)

$^{13}$C-NMR (75 MHz in CDCl$_3$) $\delta$14.2, 22.8, 23.7, 28.1, 28.5, 29.2, 31.8, 43.1, 50.8, 82.0, 166.7, 203.6

EIMS m/z (%) 242 (1 M$^+$), 186 (35), 169 (32), 127 (73), 102 (95), 57 (100)

HRMS (EI$^+$) m/z Calculation Value: C$_{14}$H$_{26}$O$_3$(M$^+$) 242.1882, Actual Measurement Value: 242.1876

Production Example B-1

Production of (R)-3-hydroxyoctanoic acid t-butyl ester

The 3-oxooctanoic acid t-butyl ester (4.50 g, 21.0 mmol) obtained in Production Example A-1 and dichloro [(R)-(+)-2,2'-bis(diphenylphosphino)-1,1'-binaphthyl]ruthenium (II) (hereunder abbreviated as (R)-BINAP-RuCl$_2$) (40 mg, 50.3 µmol) were dissolved in methanol (10 ml) freeze-degassed with liquid nitrogen. The obtained methanol solution was stirred for 42 hours using an autoclave (SUS-316; Taiatsu) at room temperature under 60 atm of hydrogen. The reaction solution was then condensed, and purified using column chromatography (silica gel: 150 g, n-hexane/ethyl acetate=10/1) to produce the target compound (4.11 g, 89%).
$[\alpha]_D^{20}$ −21.6° (c 2.1)
FT-IR (neat) 3449, 2978, 1738 cm$^{-1}$
$^1$H NMR (300 MHz in CDCl$_3$) δ0.89 (3H, t, J=6.7 Hz), 1.24-1.53 (17H, m), 2.31 (1H, dd, J=16.4 Hz, 8.9 Hz), 2.43 (1H, dd, J=16.4 Hz, 3.2 Hz), 3.10 (OH, d, J=3.9 Hz), 3.95 (1H, m)
$^{13}$C-NMR (75 MHz in CDCl$_3$) δ13.9, 22.5, 25.1, 28.0, 31.7, 36.4, 42.3, 68.0, 81.1, 172.5
CIMS m/z (%) 217 (3 M$^+$+1), 183 (8), 161 (100), 143 (25), 89 (18)
HRMS (CI$^+$) m/z Calculation Value: C$_{12}$H$_{25}$O$_3$(M$^+$+1) 217.1804, Actual Measurement Value: 217.1813

Production Example B-2

Production of (S)-3-hydroxyoctanoic acid t-butyl ester

The target compound (4.12 g, 91%) was obtained in the same manner as in Production Example B-1, except that the 3-oxooctanoic acid t-butyl ester (4.50 g, 20.9 mmol) obtained in Production Example A-1 and, as a catalyst, dichloro [(S)-(+)-2,2'-bis(diphenylphosphino)-1,1'-binaphthyl]ruthenium (II) (hereunder abbreviated as (S)-BINAP-RuCl$_2$) (40 mg, 50.3 μmol), were used.
$[\alpha]_D^{20}$ +21.3° (c 2.0)
FT-IR (neat) 3455, 2980, 1739 cm$^{-1}$
$^1$H-NMR (300 MHz in CDCl$_3$) δ0.89 (3H, t, J=6.7 Hz), 1.24-1.53 (17H, m), 2.33 (1H, dd, J=16.4 Hz, 8.9 Hz), 2.43 (1H, dd, J=16.4 Hz, 3.2 Hz), 3.10 (OH, d, J=3.7 Hz), 3.95 (1H, m)
$^{13}$C NMR (75 MHz in CDCl$_3$) δ14.0, 22.5, 25.1, 28.0, 31.7, 36.4, 42.3, 68.0, 81.0, 172.5
CIMS m/z (%) 217 (5 M$^+$+1), 183 (6), 161 (100), 143 (27), 89 (17)
HRMS (CI$^+$) m/z Calculation Value: C$_{12}$H$_{25}$O$_3$(M$^+$+1) 217.1803, Actual Measurement Value: 217.1794

Production Example B-3

Production of (R)-3-hydroxynonanoic acid t-butyl ester

The target compound (3.80 g, 94%) was obtained in the same manner as in Production Example B-1, except that the 3-oxo nonanoic acid t-butyl ester (4.00 g, 17.5 mmol) obtained in Production Example A-2 and (R)-BINAP-RuCl$_2$ (40 mg, 50.3 μmol) were used.
$[\alpha]_D^{20}$ 20.3° (c 1.0)
FT-IR (neat) 3443, 2930, 2858, 1731, 1714 cm$^{-1}$
$^1$H NMR (300 MHz in CDCl$_3$) δ0.88 (3H, t, J=7.0 Hz), 1.22-1.54 (19H, m), 2.30 (1H, dd, J=16.5 Hz, 8.9 Hz), 2.42 (1H, dd, J=16.5 Hz, 3.2 Hz), 3.09 (OH, d, J=3.7 Hz), 3.94 (1H, m)
$^{13}$C-NMR (75 MHz in CDCl$_3$) δ14.0, 22.5, 25.4, 28.1, 29.2, 31.7, 36.4, 42.3, 68.0, 81.1, 172.6
CIMS m/z (%) 231 (8 M$^+$+1), 215 (8), 197 (18), 175 (100), 157 (98), 139 (22), 127 (20), 89 (10)
HRMS (CI$^+$) m/z Calculation Value: C$_{13}$H$_{27}$O$_3$(M$^+$+1) 231.1960, Actual Measurement Value: 231.1959

Production Example B-4

Production of (S)-3-hydroxynonanoic acid t-butyl ester

The target compound (3.90 g, 96%) was obtained in the same manner as in Production Example B-1, except that the 3-oxo nonanoic acid t-butyl ester (4.00 g, 17.5 mmol) obtained in Production Example A-2 and (S)-BINAP-RuCl$_2$ (40 mg, 50.3 μmol) were used.
$[\alpha]_D^{20}$ +25.7° (c 0.9)
FT-IR (neat) 3448, 2932, 2859, 1731 cm$^{-1}$
$^1$H-NMR (300 MHz in CDCl$_3$) δ0.88 (3H, t, J=7.0 Hz), 1.22-1.57 (19H, m), 2.31 (1H, dd, J=16.2 Hz, 8.8 Hz), 2.43 (1H, dd, J=16.2 Hz, 3.2 Hz), 3.07 (OH, d, J=3.9 Hz), 3.95 (1H, m)
$^{13}$C-NMR (75 MHz in CDCl$_3$) δ14.0, 22.5, 25.3, 28.0, 29.1, 31.7, 36.4, 42.3, 68.0, 80.9, 172.4
CIMS m/z (%) 231 (10 M$^+$+1), 197 (14), 175 (100), 157 (97), 139 (25), 127 (16), 89 (10)
HRMS (CI$^+$) m/z Calculation Value: C$_{13}$H$_{27}$O$_3$(M$^+$+1) 231.1961, Actual Measurement Value: 231.1942

Production Example B-5

Production of (R)-3-hydroxydecanoic acid t-butyl ester

The target compound (4.84 g, 80%) was obtained in the same manner as in Production Example B-1, except that the 3-oxodecanoic acid t-butyl ester (6.00 g, 24.8 mmol) obtained in Production Example A-3 and (R)-BINAP-RuCl$_2$ (40 mg, 50.3 μmol) were used.
$[\alpha]_D^{20}$ −20.8° (c 1.0)
FT-IR (neat) 3445, 2934, 2857, 1732 cm$^{-1}$
$^1$H-NMR (300 MHz in CDCl$_3$) 0.88 (3H, t, J=7.0 Hz), 1.21-1.56 (21H, m), 2.31 (1H, dd, J=16.2 Hz, 8.8 Hz), 2.43 (1H, dd, J=16.2 Hz, 3.3 Hz), 3.05 (OH, d, J=3.7 Hz), 3.94 (1H, m)
$^{13}$C-NMR (75 MHz in CDCl$_3$) δ14.0, 22.5, 25.4, 28.0, 29.1, 29.4, 31.7, 36.4, 42.3, 68.0, 81.0, 172.4
CIMS m/z (%) 245 (4 M$^+$+1), 211 (8), 189 (100), 171 (84), 127 (59)
HRMS (CI$^+$) m/z Calculation Value: C$_{14}$H$_{29}$O$_3$(M$^+$+1) 245.2116, Actual Measurement Value: 245.2112

Production Example B-6

Production of (S)-3-hydroxydecanoic acid t-butyl ester

The target compound (5.12 g, 84%) was obtained in the same manner as in Production Example B-1, except that the 3-oxodecanoic acid t-butyl ester (6.00 g, 24.8 mmol) obtained in Production Example A-3 and (S)-BINAP-RuCl$_2$ (40 mg, 50.3 μmol) were used.
$[\alpha]_D^{20}$ +17.5° (c 9.0)
FT-IR (neat) 3443, 2928, 2857, 1731 cm$^{-1}$
$^1$H NMR (300 MHz in CDCl$_3$) δ0.88 (3H, t, J=6.9 Hz), 1.21-1.56 (21H, m), 2.31 (1H, dd, J=16.2 Hz, 8.8 Hz), 2.43 (1H, dd, J=16.2 Hz, 3.2 Hz), 3.06 (OH, d, J=3.7 Hz), 3.95 (1H, m)
$^{13}$C-NMR (75 MHz in CDCl$_3$) δ14.0, 22.5, 25.4, 28.0, 29.1, 29.4, 31.7, 36.4, 42.3, 68.0, 81.0, 172.4
CIMS m/z (%) 245 (45 M$^+$+1), 227 (5), 211 (10), 189 (100), 171 (45), 127 (10)
HRMS (CI$^+$) m/z Calculation Value: C$_{14}$H$_{29}$O$_3$(M$^+$+1) 245.2116, Actual Measurement Value: 245.2111

Production Example C-1

Production of (2R,3R)-2-butyl-3-hydroxyoctanoic acid t-butyl ester

A dried two-necked flask was cooled to −78° C., after which diisopropylamine (5.41 g, 53.5 mmol) was introduced thereto. Then, methyllithium (a 0.98M diethyl ether solution, 45 ml, 44.1 mmol) was added dropwise thereto, and stirred for 10 minutes. The resulting mixture was heated to 0° C., and stirred for another 30 minutes. The reaction solution was cooled to −48° C., the (R)-3-hydroxyoctanoic acid t-butyl ester (3.50 g, 16.2 mmol) obtained in Production Example B-1 was added dropwise thereto, and then the mixture was stirred for 30 minutes. To the obtained mixture was added hexamethylphosphoric triamide (HMPA) (7 ml), the mixture was stirred for one minute, then 1-iodobutane (3.87 g, 21.0 mmol) was added dropwise thereto. After the reaction solution was stirred at −48° C. for one hour, a saturated ammonium chloride solution was added thereto, and extracted 3 times with diethyl ether. The resulting organic layer was dried with anhydrous magnesium sulfate, filtered, and condensed. The obtained residue was purified by column chromatography (silica gel: 150 g, n-hexane/ethyl acetate=15/1) to produce the target compound (1.98 g, 44%).

$[\alpha]_D^{20}$ +7.2° (c 2.1)

FT-IR (neat) 3490, 2971, 1734 cm$^{-1}$ $^1$H-NMR (300 MHz in CDCl$_3$) 0.89 (3H, t, J=6.6 Hz), 0.90 (3H, t, J=6.9 Hz), 1.20-1.79 (23H, m), 2.31 (1H, dt, J=8.9 Hz, 5.4 Hz), 2.66 (OH, d, J=8.7 Hz), 3.60 (1H, m)

$^{13}$C-NMR (75 MHz in CDCl$_3$) δ13.9, 14.0, 22.6 (2C), 25.5, 28.1, 29.4, 29.5, 31.8, 35.8, 51.2, 72.5, 81.0, 175.3

CIMS m/z (%) 273 (1 M$^+$+1), 239 (10), 217 (100), 199 (92), 145 (15), 116 (15)

HRMS (CI$^+$) m/z Calculation Value: C$_{16}$H$_{33}$O$_3$(M$^+$+1) 273.2430, Actual Measurement Value: 273.2440

Production Example C-2

Production of (2S,3S)-2-butyl-3-hydroxyoctanoic acid t-butyl ester

The target compound (2.13 g, 48%) was obtained in the same manner as in Production Example C-1, except that the (5)-3-hydroxyoctanoic acid t-butyl ester (3.50 g, 16.2 mmol) obtained in Production Example B-2 was used.

$[\alpha]_D^{20}$ −6.9° (c 2.0)

FT-IR (neat) 3469, 2971, 1733 cm$^{-1}$ $^1$H-NMR (300 MHz in CDCl$_3$) δ0.89 (3H, t, J=6.6 Hz), 0.90 (3H, t, J=6.9 Hz), 1.21-1.79 (23H, m), 2.31 (1H, dt, J=8.9 Hz, 5.2 Hz), 2.66 (OH, d, J=8.7 Hz), 3.60 (1H, m)

$^{13}$C-NMR (75 MHz in CDCl$_3$) δ13.9, 14.0, 22.5 (2C), 25.4, 28.1, 29.4, 29.5, 31.8, 35.7, 51.2, 72.5, 81.0, 175.3

CIMS m/z (%) 273 (1 M$^+$+1), 239 (10), 217 (100), 199 (84), 145 (13), 116 (13)

HRMS (CI$^+$) m/z Calculation Value: C$_{16}$H$_{33}$O$_3$(M$^+$+1) 273.2430, Actual Measurement Value: 273.2428

Production Example C-3

Production of (2R,3R)-3-hydroxy-2-pentylnonanoic acid t-butyl ester

The target compound (2.49 g, 38%) was obtained in the same manner as in Production Example C-1, except that the (R)-3-hydroxynonanoic acid t-butyl ester (5.00 g, 21.7 mmol) obtained in Production Example B-3 and 1-iodopentane (5.59 g, 28.2 mmol) were used.

$[\alpha]_D^{20}$ +7.4° (c 3.4)

FT-IR (neat) 3464, 2963, 2861, 1730 cm$^{-1}$ $^1$H-NMR (300 MHz in CDCl$_3$) δ0.88 (6H, t, J=6.7 Hz), 1.20-1.78 (27H, m), 2.31 (1H, dt, J=9.6 Hz, 5.2 Hz), 2.64 (OH, d, J=8.7 Hz), 3.59 (1H, m)

$^{13}$C-NMR (75 MHz in CDCl$_3$) δ14.0, 14.1, 22.5, 22.6, 25.8, 27.0, 28.1, 29.3, 29.7, 31.7, 31.8, 35.8, 51.3, 72.5, 81.1, 175.3

CIMS m/z (%) 301 (4 M$^+$+1), 287 (5), 267 (10), 245 (100), 227 (91), 215 (10), 159 (32), 130 (35)

HRMS (CI$^+$) m/z Calculation Value: C$_{18}$H$_{37}$O$_3$(M$^+$+1) 301.2742, Actual Measurement Value: 301.2734

Production Example C-4

Production of (2S,3S)-3-hydroxy-2-pentylnonanoic acid t-butyl ester

The target compound (2.00 g, 31%) was obtained in the same manner as in Production Example C-1, except that the (R)-3-hydroxynonanoic acid t-butyl ester (5.00 g, 21.7 mmol) obtained in Production Example B-3 and 1-iodopentane (5.59 g, 28.2 mmol) were used.

$[\alpha]_D^{20}$ −8.0° (c 2.1)

FT-IR (neat) 3464, 2959, 2860, 1730, 1713 cm$^{-1}$ $^1$H-NMR (300 MHz in CDCl$_3$) δ0.88 (6H, t, J=6.6 Hz), 1.18-1.82 (27H, m), 2.32 (1H, dt, J=10.0 Hz, 5.4 Hz), 2.68 (OH, d, J=8.8 Hz), 3.60 (1H, m)

$^{13}$C-NMR (75 MHz in CDCl$_3$) δ614.0 (2C), 22.4, 22.6, 25.7, 26.9, 28.1, 29.2, 29.7, 31.6, 31.8, 35.8, 51.2, 72.4, 81.0, 175.3

CIMS m/z (%) 301 (2 M$^+$+1), 287 (5), 267 (10), 245 (100), 227 (92), 215 (10), 159 (32), 130 (33), 89 (36)

HRMS (CI$^+$) m/z Calculation Value: C$_{18}$H$_{37}$O$_3$(M$^+$+1) 301.2743, Actual Measurement Value: 301.2745

Production Example C-5

Production of (2R,3R)-2-hexyl-3-hydroxydecanoic acid t-butyl ester

The target compound (1.80 g, 33%) was obtained in the same manner as in Production Example C-1, except that the (R)-3-hydroxydecanoic acid t-butyl ester (4.00 g, 16.4 mmol) obtained in Production Example B-5 and 1-iodohexane (5.20 g, 24.5 mmol) were used.

$[\alpha]_D^{20}$ +6.4° (c 10.0)

FT-IR (neat) 3493, 2928, 2857, 1728, 1709 cm$^{-1}$ $^1$H-NMR (300 MHz in CDCl$_3$) δ0.88 (6H, t, J=6.9 Hz), 1.22-1.78 (31H, m), 2.31 (1H, dt, J=9.1 Hz, 5.2 Hz), 2.64 (OH, d, J=8.5 Hz), 3.59 (1H, m)

$^{13}$C-NMR (75 MHz in CDCl$_3$) δ14.0, 22.5, 22.6, 25.7, 27.2, 28.1, 29.1, 29.2, 29.5, 29.7, 31.6, 31.8, 35.8, 51.3, 72.5, 80.9, 175.2

CIMS m/z (%) 329 (25 M$^+$+1), 311 (5), 273 (100), 255 (86), 237 (6), 213 (5), 173 (17), 144 (21)

HRMS (CI$^+$) m/z Calculation Value: C$_{20}$H$_{41}$O$_3$(M$^+$+1) 329.3056, Actual Measurement Value: 329.3056

Production Example C-6

Production of (2S,3S)-2-hexyl-3-hydroxydecanoic acid t-butyl ester

The target compound (2.20 g, 41%) was obtained in the same manner as in Production Example C-1, except that the (S)-3-hydroxydecanoic acid t-butyl ester (4.00 g, 16.4 mmol) obtained in Production Example B-6 and 1-iodohexane (5.20 g, 24.5 mmol) were used.

[α]$_D^{20}$ −7.1° (c 10.0)

FT-IR (neat) 3497, 2929, 2857, 1728, 1708 cm$^{-1}$ $^1$H-NMR (300 MHz in CDCl$_3$) 0.88 (6H, t, J=6.9 Hz), 1.22-1.78 (31H, m), 2.31 (1H, dt, J=9.1 Hz, 5.2 Hz), 2.64 (OH, d, J=8.5 Hz), 3.59 (1H, m)

$^{13}$C-NMR (75 MHz in CDCl$_3$) δ14.0, 22.5, 22.6, 25.8, 27.2, 28.1, 29.1, 29.2, 29.5, 29.7, 31.6, 31.8, 35.8, 51.3, 72.5, 81.0, 175.3

CIMS m/z (%) 329 (20 M$^+$+1), 295 (8), 273 (100), 255 (90), 237 (5), 173 (10), 144 (11)

HRMS (CI$^+$) m/z Calculation Value: C$_{20}$H$_{43}$O$_3$(M$^+$+1) 329.3056, Actual Measurement Value: 329.3050

Production Example C-7-1

Production of (2R,3S)-3-benzoyloxy-2-pentylnonanoic acid t-butyl ester

The (2R,3R)-3-hydroxy-2-pentylnonanoic acid t-butyl ester (1.00 g, 3.33 mmol) obtained in Production Example C-3 was dissolved in anhydrous toluene (18 ml), and then cooled to 0° C. Benzoic acid (813 mg, 6.66 mmol), triphenylphosphine (2.01 g, 7.66 mmol), and diisopropyl azodicarboxylate (hereunder abbreviated as "DIAD") (a 40 w/v % toluene solution: 3.87 ml, 7.66 mmol) were sequentially added to the resulting mixture to be stirred for two hours. To the reaction mixture was added an aqueous saturated sodium hydrogen solution, which was extracted 3 times with diethyl ether. The resulting organic layer was dried with anhydrous magnesium sulfate, filtered, and condensed. The obtained residue was purified by column chromatography (silica gel: 40 g, n-hexane/ethyl acetate=15/1) to produce the target compound (1.28 g, 95%).

[α]$_D^{20}$ −0.26° (c 28, CHCl$_3$)

FT-IR (neat) 3090, 3063, 3033, 2957, 2859, 1733 cm$^{-1}$ $^1$H-NMR (300 MHz in CDCl$_3$) δ0.86 (6H, m), 1.18-1.57 (25H, m), 1.69 (2H, m), 2.64 (1H, ddd, J=10.7 Hz, 7.0 Hz, 3.7 Hz), 5.28 (1H, ddd, J=8.1 Hz, 7.0 Hz, 4.1 Hz), 7.45 (2H, m), 7.57 (1H, tt, J=6.5 Hz, 1.4 Hz), 8.05 (2H, m)

$^{13}$C-NMR (75 MHz in CDCl$_3$) δ14.0 (2C), 22.5 (2C), 25.3, 27.1, 28.0, 28.4, 29.1, 31.6, 31.8, 50.6, 75.0, 80.6, 128.3, 129.6, 130.4, 132.9, 166.0, 172.5

CIMS m/z (%) 405 (12 M$^+$+1), 349 (100), 331 (21), 278 (15), 262 (8), 227 (85), 226 (60), 209 (33), 182 (20), 123 (19), 105 (59)

HRMS (CI$^+$) m/z Calculation Value: C$_{25}$H$_{41}$O$_4$(M$^+$+1)- 405.3005, Actual Measurement Value: 405.2991

Production Example C-7-2

Production of (2R,3S)-3-hydroxy-2-pentylnonanoic acid t-butyl ester

The (2R,3S)-3-benzoyloxy-2-pentylnonanoic acid t-butyl ester (1.24 g, 3.06 mmol) obtained in Production Example C-7-1 was dissolved in anhydrous toluene (4 ml), and then tributyltin oxide (2.34 g, 3.92 mmol) was added thereto to be refluxed with heating. Then, 39 hours later, distilled water was added to the reaction mixture, and extracted 3 times with diethyl ether. The resulting organic layer was dried with anhydrous magnesium sulfate, filtered, and condensed. The obtained residue was purified by column chromatography (silica gel: 30 g, n-hexane/ethyl acetate=20/1), and the target compound (501 mg, 54%) was obtained.

[α]$_D^{20}$ +2.7° (c 2.4)

FT-IR (neat) 3435, 2957, 2931, 2859, 1726 cm$^{-1}$ $^1$H-NMR (300 MHz in CDCl$_3$) δ0.88 (6H, m), 1.14-1.72 (27H, m), 2.30 (1H, dt, J=10.2 Hz, 4.4 Hz), 2.51 (OH, d, J=4.4 Hz), 3.74 (1H, dt, J=8.4 Hz, 4.4 Hz)

$^{13}$C-NMR (75 MHz in CDCl$_3$) δ14.0, 14.1, 22.5, 22.6, 25.8, 26.9, 27.3, 28.1, 29.2, 31.7, 31.8, 34.3, 51.7, 72.2, 80.9, 175.1

CIMS m/z (%) 301 (3 M$^+$+1), 287 (4), 267 (14), 245 (95), 227 (100), 186 (10), 159 (15), 130 (85), 113 (10)

HRMS (CI$^+$) m/z Calculation Value: CO$_{37}$O$_3$ (M$^+$+1) 301.2743, Actual Measurement Value: 301.2739

Production Example C-8-1

Production of (2S,3R)-3-benzoyloxy-2-pentylnonanoic acid t-butyl ester

The target compound (1.23 g, 91%) was obtained in the same manner as in Production Example C-7-1, except that the (2S,3S)-3-hydroxy-2-pentylnonanoic acid t-butyl ester (1.00 g, 3.33 mmol) obtained in Production Example C-4 was used.

[α]$_D^{20}$ +0.25° (c 10, CHCl$_3$)

FT-IR (neat) 3089, 3063, 3032, 2958, 2860, 1733 cm$^{-1}$ $^1$H-NMR (300 MHz in CDCl$_3$) δ0.86 (6H, m), 1.18-1.56 (25H, m), 1.69 (2H, m), 2.64 (1H, ddd, J=10.7 Hz, 7.0 Hz, 3.7 Hz), 5.28 (1H, ddd, J=8.5 Hz, 7.2 Hz, 4.3 Hz), 7.45 (2H, m), 7.57 (1H, tt, J=7.3 Hz, 1.4 Hz), 8.05 (2H, m)

$^{13}$C-NMR (75 MHz in CDCl$_3$) δ13.9, 14.0, 22.4, 22.5, 25.3, 27.1, 28.0, 28.4, 29.1, 31.6, 31.8, 50.6, 75.0, 80.6, 128.3, 129.6, 130.4, 132.9, 166.0, 172.5

CIMS m/z (%) 405 (14 M$^+$+1), 349 (100), 331 (21), 278 (13), 227 (80), 209 (30), 182 (16), 112 (20), 105 (49)

HRMS (CI$^+$) m/z Calculation Value: C$_{25}$H$_{41}$O$_4$(M$^+$+1) 405.3005, Actual Measurement Value: 405.2999

Production Example C-8-2

Production of (2S,3R)-3-hydroxy-2-pentylnonanoic acid t-butyl ester

The target compound (680 mg, 54%) was obtained in the same manner as in Production Example C-7-2, except that the (2S,3R)-3-benzoyloxy-2-pentylnonanoic acid t-butyl ester (1.72 g, 4.25 mmol) obtained in Production Example C-8-1 was used.

[α]$_D^{20}$ −3.3° (c 2.2)

FT-IR (neat) 3437, 2967, 2864, 1731 cm$^{-1}$ $^1$H-NMR (300 MHz in CDCl$_3$) δ0.88 (6H, m), 1.18-1.72 (27H, m), 2.30 (1H, dt, J=10.3 Hz, 4.4 Hz), 2.51 (OH, d, J=4.4 Hz), 3.74 (1H, dt, J=8.7 Hz, 4.4 Hz)

$^{13}$C-NMR (75 MHz in CDCl$_3$) δ14.0 (2C), 22.5, 22.6, 25.8, 27.0, 27.3, 28.1, 29.2, 31.7, 31.8, 34.3, 51.7, 72.2, 80.9, 175.1

CIMS m/z (%) 301 (2 M$^+$+1), 267 (15), 245 (82), 227 (100), 186 (8), 159 (10), 130 (65), 113 (10)

HRMS (CI$^+$) m/z Calculation Value: C$_{18}$H$_{37}$O$_3$(M$^+$+1) 301.2742, Actual Measurement Value: 301.2735

Production Example C-9

Production of (2R,3R)-3-methoxy-2-pentylnonanoic acid t-butyl ester

The (2R,3R)-3-hydroxy-2-pentylnonanoic acid t-butyl ester (500 mg, 1.66 mmol) obtained in Production Example C-3 was dissolved in anhydrous dichloromethane (5.0 ml).

Then, 2,6-di-t-butylpyridine (476 mg, 2.49 mmol) was added thereto to be stirred for 5 minutes at room temperature. Methyl triflate (328 mg, 1.99 mmol) was added to the obtained mixture, which was heated to 40° C. and stirred for 20 hours. An aqueous saturated ammonium chloride solution was added to the reaction solution, which was extracted 3 times with dichloromethane. The resulting organic layer was dried with anhydrous magnesium sulfate, filtered, and condensed. The obtained residue was purified by column chromatography (silica gel: 25 g, n-hexane/ethyl acetate=20/1) to produce the target compound (498 mg, 95%).

$[\alpha]_D^{20}$ +7.8° (c 2.5)

FT-IR (neat) 2963, 2863, 1733 cm$^{-1}$ $^1$H-NMR (300 MHz in CDCl$_3$) δ0.88 (6H, m), 1.18-1.66 (27H, m), 2.44 (1H, m), 3.33 (3H, s), 3.34 (1H, m)

$^{13}$C-NMR (75 MHz in CDCl$_3$) δ14.0 (2C), 22.5, 22.6, 24.6, 27.2, 27.8, 28.1, 29.5, 30.7, 31.7, 31.8, 50.4, 57.6, 80.0, 82.4, 174.0

CIMS m/z (%) 315 (3 M$^+$+1), 301 (4), 259 (92), 241 (100), 227 (34), 186 (28), 173 (15), 129 (92)

HRMS (CI) m/z Calculation Value: C$_{19}$H$_{39}$O$_3$(M$^+$+1) 315.2899, Actual Measurement Value: 315.2884

Production Example D-1

Production of (2R,3R)-3-benzyloxy-2-butyloctanoic acid

The (2R,3R)-2-butyl-3-hydroxyoctanoic acid t-butyl ester (1.00 g, 3.67 mmol) obtained in Production Example C-1 was dissolved in anhydrous dichloromethane (12 ml). Triethylamine (1.37 g, 13.6 mmol) and trimethylchlorosilane (1.20 g, 11.0 mmol) were added to this solution, which was stirred for 30 minutes at room temperature. Then, distilled water was added thereto, and extracted 3 times with dichloromethane. The resulting organic layer was dried with anhydrous magnesium sulfate, filtered, and condensed. The crude product was dissolved in anhydrous dichloromethane (69 ml), and then cooled to −48° C. Benzaldehyde (584 mg, 5.51 mmol), triethylsilane (641 mg, 5.51 mmol), and trimethylsilyl triflate (408 mg, 1.84 mmol) were sequentially added thereto; the mixture was stirred at −48° C. for 15 minutes, and then warmed to room temperature. After the reaction of 2 hours, an aqueous saturated sodium hydrogen solution was added thereto to be washed. The resulting organic layer was dried with anhydrous magnesium sulfate, filtered, and condensed. The obtained residue was purified by column chromatography (silica gel: 30 g, n-hexane/ethyl acetate=7/1) to produce the target compound (781 mg, 70%).

$[\alpha]_D^{20}$ −1.5° (c 5.0)

FT-IR (neat) 3088, 3064, 3032, 2956, 2861, 1710 cm$^{-1}$ $^1$H-NMR (300 MHz in CDCl$_3$) δ0.88 (6H, t, J=6.9 Hz), 1.20-1.73 (14H, m), 2.66 (1H, ddd, J=10.3 Hz, 5.9 Hz, 5.6 Hz), 3.65 (1H, q, J=5.9 Hz), 4.52 (1H, d, J=11.4 Hz), 4.61 (1H, d, J=11.4 Hz), 7.25-7.36 (5H, m)

$^{13}$C-NMR (75 MHz in CDCl$_3$) δ13.9, 14.0, 22.6 (2C), 24.4, 27.5, 29.8, 31.0, 31.9, 49.7, 72.1, 79.9, 127.7, 127.9, 128.3, 138.1, 180.1

CIMS m/z (%) 307 (85 M$^+$+1), 298 (100), 271 (18), 243 (12), 199 (30), 171 (10), 133 (10), 91 (90)

HRMS (CI$^+$) m/z Calculation Value: C$_{19}$H$_{31}$O$_3$(M$^+$+1) 307.2273, Actual Measurement Value: 307.2266

Production Example D-2

Production of (2S,3S)-3-benzyloxy-2-butyloctanoic acid

The target compound (740 mg, 66%) was obtained in the same manner as in Production Example D-1, except that the (2S,3S)-2-butyl-3-hydroxyoctanoic acid t-butyl ester (1.00 g, 3.67 mmol) obtained in Production Example C-2 was used.

$[\alpha]_D^{20}$ −1.5° (c 5.0)

FT-IR (neat) 3088, 3064, 3032, 2962, 2871, 1713 cm$^{-1}$ $^1$H-NMR (300 MHz in CDCl$_3$) δ0.88 (6H, t, J=6.9 Hz), 1.99-1.72 (14H, m), 2.66 (1H, ddd, J=10.5 Hz, 6.1 Hz, 5.8 Hz), 3.65 (1H, q, J=5.8 Hz), 4.52 (1H, d, J=11.4 Hz), 4.60 (1H, d, J=11.4 Hz), 7.25-7.36 (5H, m)

$^{13}$C-NMR (75 MHz in CDCl$_3$) δ13.9, 14.0, 22.6 (2C), 24.4, 27.4, 29.8, 31.0, 31.9, 49.7, 72.1, 79.9, 127.6, 127.8, 128.3, 138.1, 180.3

CIMS m/z (%) 307 (88 M$^+$+1), 298 (100), 271 (20), 243 (15), 199 (23), 191 (10), 133 (12), 91 (85)

HRMS (CI$^+$) m/z Calculation Value: C$_{19}$H$_{31}$O$_3$(M$^+$+1) 307.2273, Actual Measurement Value: 307.2270

Production Example D-3

Production of (2R,3R)-3-benzyloxy-2-pentylnonanoic acid

The target compound (820 mg, 74%) was obtained in the same manner as in Production Example D-1, except that the (2R,3R)-3-hydroxy-2-pentylnonanoic acid t-butyl ester (1.00 g, 3.33 mmol) obtained in Production Example C-3 was used.

$[\alpha]_D^{20}$ +7.5° (c 2.5)

FT-IR (neat) 3031, 2959, 2861, 1945, 1866, 1806, 1713 cm$^{-1}$ $^1$H-NMR (300 MHz in CDCl$_3$) δ0.88 (6H, m), 1.18-1.74 (18H, m), 2.66 (1H, ddd, J=10.2 Hz, 5.8 Hz, 4.4 Hz), 3.64 (1H, q, J=5.8 Hz), 4.52 (1H, d, J=11.3 Hz), 4.60 (1H, d, J=11.3 Hz), 7.22-7.40 (5H, m)

$^{13}$C-NMR (75 MHz in CDCl$_3$) δ13.9, 14.0, 22.3, 22.5, 24.6, 27.2, 27.5, 29.3, 30.9, 31.7 (2C), 49.7, 72.0, 79.9, 127.6, 127.9, 128.3, 138.2, 180.7

CIMS m/z (%) 335 (52 M$^+$+1), 317 (70), 299 (10), 228 (37), 182 (18), 157 (10), 133 (10), 107 (35), 91 (100)

HRMS (CI$^+$) m/z Calculation Value: C$_{21}$H$_{35}$O$_3$(M$^+$+1) 335.2586, Actual Measurement Value: 335.2577

Production Example D-4

Production of (2S,3S)-3-benzyloxy-2-pentylnonanoic acid

The target compound (966 mg, 87%) was obtained in the same manner as in Production Example D-1, except that the (2S,3S)-3-hydroxy-2-pentylnonanoic acid t-butyl ester (1.00 g, 3.33 mmol) obtained in Production Example C-4 was used.

$[\alpha]_D^{20}$ −6.7° (c 2.5)

FT-IR (neat) 3031, 2957, 2860, 1945, 1867, 1805, 1713 cm$^{-1}$ $^1$H-NMR (300 MHz in CDCl$_3$) δ0.88 (6H, m), 1.18-1.74 (18H, m), 2.64 (1H, ddd, J=10.2 Hz, 5.1 Hz, 4.4 Hz), 3.63 (1H, q, J=5.1 Hz), 4.53 (1H, d, J=11.4 Hz), 4.64 (1H, d, J=11.4 Hz), 7.29-7.39 (5H, m)

$^{13}$C-NMR (75 MHz in CDCl$_3$) δ14.0, 14.1, 22.4, 22.6, 24.7, 27.3, 27.7, 29.4, 31.1, 31.7, 31.8, 49.7, 72.1, 79.9, 127.6, 127.8, 128.3, 138.1, 180.3

CIMS m/z (%) 335 (68 M$^+$+1), 317 (85), 299 (12), 228 (36), 182 (19), 157 (10), 133 (13), 107 (31), 91 (100)

HRMS (CI⁺) m/z Calculation Value: $C_{21}H_{35}O_3$ (M⁺+1) 335.2586, Actual Measurement Value: 335.2580

Production Example D-5

Production of (2R,3R)-3-benzyloxy-2-hexyldecanoic acid

The target compound (522 mg, 64%) was obtained in the same manner as in Production Example D-1, except that the (2R,3R)-2-hexyl-3-hydroxydecanoic acid t-butyl ester (700 mg, 2.26 mmol) obtained in Production Example C-5 was used.

$[\alpha]_D^{20}$ +1.3° (c 2.2)
FT-IR (neat) 3087, 3064, 3031, 2931, 2857, 1708 cm⁻¹
¹H-NMR (300 MHz in CDCl₃) δ0.88 (6H, m), 1.16-1.42 (18H, m), 1.59 (4H, m), 2.65 (1H, dt, J=10.5 Hz, 5.1 Hz), 3.64 (1H, q, J=5.6 Hz), 4.52 (1H, d, J=11.1 Hz), 4.61 (1H, d, J=11.1 Hz), 7.23-7.38 (5H, m)
¹³C-NMR (75 MHz in CDCl₃) δ14.0, 19.1, 22.6 (2C), 24.8, 27.6, 27.7, 29.2, 29.6, 31.1, 31.6, 31.8, 49.7, 72.1, 79.9, 127.6, 127.8, 128.3, 138.1, 180.1
CIMS m/z (%) 363 (100 M⁺+1), 345 (91), 327 (11), 255 (15), 199 (7), 107 (8), 91 (34)
HRMS (CI⁺) m/z Calculation Value: $C_{23}H_{39}O_3$ (M⁺+1) 363.2899, Actual Measurement Value: 363.2904

Production Example D-6

Production of (2S,3S)-3-benzyloxy-2-hexyldecanoic acid

The target compound (621 mg, 76%) was obtained in the same manner as in Production Example D-1, except that the (2S,3S)-2-hexyl-3-hydroxydecanoic acid t-butyl ester (700 mg, 2.26 mmol) obtained in Production Example C-6 was used.

$[\alpha]_D^{20}$ −1.8° (c 2.2)
FT-IR (neat) 3088, 3069, 3031, 2930, 2858, 1709 cm⁻¹
¹H-NMR (300 MHz in CDCl₃) 0.88 (6H, m), 1.16-1.42 (18H, m), 1.59 (4H, m), 2.65 (1H, dt, J=10.5 Hz, 5.1 Hz), 3.64 (1H, q, J=5.8 Hz), 4.52 (1H, d, J=11.3 Hz), 4.61 (1H, d, J=11.3 Hz), 7.23-7.38 (5H, m)
¹³C-NMR (75 MHz in CDCl₃) δ14.0, 14.1, 22.6 (2C), 24.8, 27.6, 27.7, 29.2, 29.6, 31.1, 31.6, 31.8, 49.7, 72.1, 79.9, 127.6, 127.8, 128.3, 138.1, 180.1
CIMS m/z (%) 363 (90 M⁺+1), 345 (100), 327 (15), 299 (10), 255 (22), 199 (8), 133 (9), 91 (38)
HRMS (CI⁺) m/z Calculation Value: $C_{23}H_{39}O_3$ (M⁺+1) 363.2899, Actual Measurement Value: 363.2892

Production Example D-7

Production of (2R,3S)-3-benzyloxy-2-pentylnonanoic acid

The target compound (378 mg, 68%) was obtained in the same manner as in Production Example D-1, except that the (2R,3S)-3-hydroxy-2-pentylnonanoic acid t-butyl ester (500 mg, 1.66 mmol) obtained in Production Example C-7-2 was used.

$[\alpha]_D^{20}$ −16.3° (c 2.9)
FT-IR (neat) 3064, 3032, 2959, 2861, 1946, 1867, 1712 cm⁻¹
¹H-NMR (300 MHz in CDCl₃) δ0.88 (6H, m), 1.16-1.84 (18H, m), 2.67 (1H, dt, J=9.9 Hz, 5.2 Hz), 3.62 (1H, q, J=5.2 Hz), 4.56 (1H, d, J=11.3 Hz), 4.63 (1H, d, J=11.3 Hz), 7.26-7.46 (5H, m)
¹³C-NMR (75 MHz in CDCl₃) δ13.9, 14.0, 22.4, 22.5, 25.3, 27.4, 27.9, 29.2, 31.7, 49.2, 72.1, 79.8, 127.8, 128.1, 128.5, 138.1, 180.3
CIMS m/z (%) 335 (31 M⁺+1), 317 (52), 299 (9), 228 (24), 227 (22), 182 (12), 107 (25), 91 (100)
HRMS (CI⁺) m/z Calculation value: $C_{21}H_{35}O_3$(M⁺1) 335.2586, Actual Measurement Value: 335.2588

Production Example D-8

Production of (2S,3R)-3-benzyloxy-2-pentylnonanoic acid

The target compound (470 mg, 84%) was obtained in the same manner as in Production Example D-1, except that the (2S,3R)-3-hydroxy-2-pentylnonanoic acid t-butyl ester (500 mg, 1.66 mmol) obtained in Production Example C-8-2 was used.

$[\alpha]_D^{20}$ +16.5° (c 2.2)
FT-IR (neat) 3064, 3031, 2958, 2861, 1945, 1867, 1805, 1713 cm⁻¹
¹H-NMR (300 MHz in CDCl₃) δ0.88 (6H, m), 1.16-1.84 (18H, m), 2.67 (1H, dt, J=9.9 Hz, 5.2 Hz), 3.62 (1H, q, J=5.2 Hz), 4.56 (1H, d, J=11.3 Hz), 4.63 (1H, d, J=11.3 Hz), 7.28-7.44 (5H, m)
¹³C-NMR (75 MHz in CDCl₃) δ14.0, 14.1, 22.4, 22.6, 25.4, 27.5, 27.9, 29.3, 31.7, 49.2, 72.1, 79.8, 127.8, 128.0, 128.4, 138.1, 180.2
CIMS m/z (%) 335 (42 M⁺+1), 317 (80), 299 (10), 228 (40), 227 (30), 182 (18), 157 (10), 133 (10), 91 (100)
HRMS (CI⁺) m/z Calculation Value: $C_{21}H_{35}O_3$(M⁺+1) 335.2586, Actual Measurement Value: 335.2582

Production Example D-9

Production of (2R,3R)-3-methoxy-2-pentylnonanoic acid

The (2R,3R)-3-methoxy-2-pentylnonanoic acid t-butyl ester (450 mg, 1.43 mmol) obtained in Production Example C-9 was dissolved in anhydrous dichloromethane (10 ml), then cooled to 0° C. While the obtained solution was stirred, trimethylsilyl triflate (162 mg, 729 μmol) was added dropwise thereto. After a five-minute stirring, the solution was cooled to room temperature. After the reaction of 30 minutes, an aqueous saturated sodium bicarbonate solution was added thereto to be washed. The resulting organic layer was dried with anhydrous magnesium sulfate, filtered, and condensed. The obtained residue was purified by column chromatography (silica gel: 15 g, n-hexane/ethyl acetate=3/1) to produce the target compound (341 mg, 92%).

$[\alpha]_D^{20}$ +21.3°(c 1.1)
FT-IR (neat) 2956, 2933, 2860, 1708 cm⁻¹
¹H-NMR (300 MHz in CDCl₃) δ0.88 (6H, m), 1.20-1.72 (18H, m), 2.58 (1H, ddd, J=10.2 Hz, 5.6 Hz, 4.7 Hz), 3.38 (1H, m), 3.41 (3H, s)
¹³C-NMR (75 MHz in CDCl₃) δ14.0, 14.1, 22.4, 22.6, 24.7, 27.3, 27.9, 29.4, 30.8, 31.7, 31.8, 49.6, 57.9, 82.0, 179.8
CIMS m/z (%) 259 (17 M⁺+1), 241 (100), 227 (29), 209 (20), 129 (74), 97 (21)
HRMS (CI⁺) m/z Calculation Value: $C_{15}H_{31}O_3$(M⁺+1) 259.2273, Actual Measurement Value: 259.2268

Production Example E-1

Production of 6,6'-bis-O-[(2R,3R)-3-benzyloxy-2-pentylnonanoyl]-2,3,4,2',3',4'-hexabenzyl-α,α'-trehalose The (2R,3R)-3-benzyloxy-2-pentylnonanoic acid (100 mg, 299 μmol) obtained in Production Example D-3 and a trehalose compound (2,3,4,2',3',4'-hexabenzyloxy-α,α'-trehalose) (115 mg, 130 μmol) were dissolved in anhydrous dichloromethane (3 ml). Powdered molecular sieves 4A, 4-dimethylaminopyridine (15.8 mg, 130 μmol), and 1-ethyl-3-(3-diethylaminopropyl) carbodiimide hydrochloride (hereunder abbreviated as EDCI) (74.6 mg, 389 μmol) were sequentially added thereto, and reacted at room temperature for 6 hours. The reaction mixture was filtered using Celite 535. Distilled water was added to the obtained filtrate, which was then extracted 3 times with dichloromethane. The resulting organic layer was dried with anhydrous magnesium sulfate, filtered, and condensed. The obtained residue was purified by column chromatography (silica gel: 15 g, n-hexane/ethyl acetate=9/1) to produce the target compound (168 mg, 85%).

$[\alpha]_D^{20}$ +91.9° (c 0.5)

FT-IR (neat) 3088, 3063, 3031, 2929, 2858, 1949, 1871, 1807, 1738 $cm^{-1}$ $^1$H-NMR (300 MHz in $CDCl_3$) δ0.83 (12H, m), 1.10-1.68 (36H, m), 2.66 (2H, ddd, J=10.6 Hz, 7.2 Hz, 3.7 Hz), 3.49 (2H, dd, J=9.6 Hz, 3.6 Hz), 3.55 (2H, t, J=9.5 Hz), 3.62 (2H, m), 4.01 (2H, t, J=9.5 Hz), 4.09 (2H, dd, J=12.8 Hz, 3.6 Hz), 4.19 (4H, m), 4.46 (4H, s), 4.52 (2H, d, J=10.6 Hz), 4.61 (2H, d, J=11.8 Hz), 4.67 (2H, d, J=11.8 Hz), 4.84 (4H, d, J=11.1 Hz), 4.99 (2H, d, J=10.9 Hz), 5.10 (2H, d, J=3.7 Hz), 7.19-7.37 (40H, m)

$^{13}$C-NMR (75 MHz in $CDCl_3$) δ14.0, 14.1, 22.4, 22.6, 24.9, 27.5, 29.4, 31.1, 31.8, 49.8, 62.2, 69.1, 71.8, 72.9, 75.2, 75.6, 77.2, 77.7, 79.6, 80.2, 81.5, 93.9, 127.4, 127.6, 127.7, 127.8, 127.9, 128.2, 128.4 (3C), 137.8, 138.0, 138.6, 138.7, 174.3

FABMS m/z (%) 1538 (2 M$^+$+Na), 750 (2), 642 (10), 551 (19), 443 (12))$^{x25}$, 209 (4), 181 (41), 91 (100)

HRMS (FAB$^+$) m/z Calculation Value: $C_{96}H_{122}O_{15}Na$ (M$^+$+Na) 1537.8681, Actual Measurement Value: 1537.8657

Production Example E-2

Production of 6,6'-bis-O-[(2S,3S)-3-benzyloxy-2-pentylnonanoyl]-2,3,4,2',3',4'-hexabenzyl-α,α'-trehalose The target compound (151 mg, 77%) was obtained in the same manner as in Production Example E-1, except that the (2S,3S)-3-benzyloxy-2-pentylnonanoic acid (100 mg, 299 μmol) obtained in Production Example D-4 was used.

$[\alpha]_D^{20}$ +74.1°(c 0.3)

FT-IR (neat) 3088, 3063, 3031, 2929, 2858, 1949, 1869, 1807, 1738 $cm^{-1}$ $^1$H-NMR (300 MHz in $CDCl_3$) 0.84 (12H, m), 1.10-1.68 (36H, m), 2.69 (2H, ddd, J=10.7 Hz, 7.0 Hz, 3.4 Hz), 3.50 (2H, m), 3.55 (2H, m), 3.62 (2H, m), 4.00 (2H, t, J=9.4 Hz), 4.06 (2H, dd, J=12.2 Hz, 2.6 Hz), 4.21 (4H, m), 4.44 (4H, m), 4.46 (4H, m), 4.64 (2H, d, J=12.1 Hz), 4.70 (2H, d, J=12.1 Hz), 4.75 (2H, d, J=10.5 Hz), 4.84 (2H, d, J=10.9 Hz), 4.98 (2H, d, J=10.9 Hz), 5.08 (2H, d, J=3.4 Hz), 7.14-7.38 (40H, m)

$^{13}$C-NMR (75 MHz in $CDCl_3$) δ14.1 (2C), 22.5, 22.6, 24.8, 27.4, 27.6, 29.5, 31.0, 31.8, 49.7, 62.1, 69.1, 71.8, 72.9, 75.3, 75.7, 77.7, 79.5, 80.0, 81.5, 94.0, 127.4, 127.6, 127.7, 127.8, 127.9, 128.0, 128.2, 128.3, 128.4 (2C), 128.5, 137.8, 137.9, 138.5, 138.7, 174.2

FABMS m/z (%) 1538 (2 M$^+$+Na), 750 (2), 641 (7), 443 (10)$^{x25}$, 181 (29), 91 (100)

HRMS (FAB$^+$) m/z Calculation Value: $C_{96}H_{122}O_{15}Na$ (M$^+$+Na) 1537.8681, Actual Measurement Value: 1537.8657

Production Example E-3

Production of 6,6'-bis-O-[(2R,3S)-3-benzyloxy-2-pentylnonanoyl]-2,3,4,2',3',4'-hexabenzyl-α,α'-trehalose The target compound (173 mg, 87%) was obtained in the same manner as in Production Example E-1, except that the (2R,3S)-3-benzyloxy-2-pentylnonanoic acid (100 mg, 299 μmol) obtained in Production Example D-7 was used.

$[\alpha]_D^{20}$ +82.1° (c 0.5)

FT-IR (neat) 3088, 3063, 3031, 2953, 2928, 2858, 1950, 1874, 1807, 1736 $cm^{-1}$ $^1$H-NMR (300 MHz in $CDCl_3$) 0.83 (12H, m), 1.10-1.76 (36H, m), 2.65 (2H, ddd, J=10.4 Hz, 6.6 Hz, 4.1 Hz), 3.49 (2H, dd, J=9.6 Hz, 3.6 Hz), 3.54 (2H, m), 3.59 (2H, t, J=9.8 Hz), 4.02 (2H, t, J=9.3 Hz), 4.08 (2H, dd, J=12.2 Hz, 2.5 Hz), 4.18 (4H, m), 4.45 (2H, d, J=11.3 Hz), 4.52 (2H, d, J=10.6 Hz), 4.54 (2H, d, J=11.3 Hz), 4.62 (2H, d, J=11.8 Hz), 4.68 (2H, d, J=11.8 Hz), 4.84 (4H, d, J=10.7 Hz), 4.98 (2H, d, J=10.7 Hz), 5.09 (2H, d, J=3.6 Hz), 7.19-7.36 (40H, m)

$^{13}$C-NMR (75 MHz in $CDCl_3$) δ14.0, 14.1, 22.5, 22.6, 25.3, 27.6, 28.4, 29.4, 31.8, 32.1, 49.9, 62.1, 69.1, 71.9, 73.1, 75.2, 75.7, 77.8, 79.8, 80.0, 81.5, 93.8, 127.4, 127.5, 127.6, 127.7, 127.8, 127.9 (2C), 128.3, 128.4 (2C), 128.5, 137.8, 138.0, 138.5, 138.7, 174.1

FABMS m/z (%) 1538 (1 M$^+$+Na), 642 (4), 443 (9))$^{x25}$, 181 (28), 91 (100)

HRMS (FAB$^+$) m/z Calculation value: $C_{96}H_{122}O_{15}Na$ (M$^+$+Na) 1537.8681, Actual Measurement Value: 1537.8658

Production Example E-4

Production of 6,6'-bis-O-[(2S,3R)-3-benzyloxy-2-pentylnonanoyl]-2,3,4,2',3',4'-hexabenzyl-α,α'-trehalose The target compound (179 mg, 91%) was obtained in the same manner as in Production Example E-1, except that the (2S,3R)-3-benzyloxy-2-pentylnonanoic acid (100 mg, 299 μmol) obtained in Production Example D-8 was used.

$[\alpha]_D^{20}$ +87.3° (c 0.4)

FT-IR (neat) 3088, 3063, 3031, 2953, 2928, 2858, 1949, 1869, 1808, 1734 $cm^{-1}$ $^1$H-NMR (300 MHz in $CDCl_3$) δ0.82 (12H, m), 1.10-1.74 (36H, m), 2.70 (2H, ddd, J=10.7 Hz, 6.5 Hz, 4.4 Hz), 3.45 (2H, dd, J=9.6 Hz, 3.6 Hz), 3.52 (2H, m), 3.55 (2H, t, J=9.6 Hz), 4.00 (2H, t, J=9.4 Hz), 4.10 (2H, dd, J=12.8 Hz, 3.3 Hz), 4.18 (4H, m), 4.45 (2H, d, J=11.4 Hz), 4.53 (2H, d, J=10.6 Hz), 4.58 (2H, d, J=11.4 Hz), 4.61 (2H, d, J=11.8 Hz), 4.68 (2H, d, J=11.8 Hz), 4.79 (2H, d, J=10.6 Hz), 4.83 (2H, d, J=10.9 Hz), 4.96 (2H, d, J=10.9 Hz), 5.13 (2H, d, J=3.6 Hz), 7.19-7.34 (40H, m)

$^{13}$C-NMR (75 MHz in $CDCl_3$) δ14.0, 14.1, 22.5, 22.6, 25.4, 27.5, 28.8, 29.4, 31.8, 32.0, 49.6, 62.1, 69.1, 71.8, 73.0, 75.2, 75.6, 77.7, 79.6, 80.2, 81.5, 94.0, 127.4, 127.5, 127.6, 127.7 (2C), 127.8, 127.9 (2C), 128.4 (3C), 128.5, 137.9, 138.1, 138.4, 138.7, 174.1

FABMS m/z (%) 1538 (1 M$^+$+Na), 749 (2), 641 (8), 551 (11), 443 (8))[x25], 181 (25), 91 (100)
HRMS (FAB$^+$) m/z Calculation Value: $C_{96}H_{122}O_{15}Na$ (M$^+$+Na) 1537.8681, Actual Measurement Value: 1537.8657

Production Example E-5

Production of 6,6'-bis-O-[(2R,3R)-3-benzyloxy-2-hexyldecanoyl]-2,3,4,2',3',4'-hexabenzyl-α,α'-trehalose The target compound (164 mg, 61%) was obtained in the same manner as in Production Example E-1, except that the (2R,3R)-3-benzyloxy-2-hexyldecanoic acid (136 mg, 374 μmol) obtained in Production Example D-5 was used.
$[α]_D^{20}$ +83.0° (c 0.2)
FT-IR (neat) 3088, 3063, 3031, 2927, 2857, 1949, 1872, 1806, 1737 cm$^{-1}$
$^1$H-NMR (300 MHz in CDCl$_3$) δ0.80 (6H, t, J=7.2 Hz), 0.86 (6H, t, J=7.0 Hz), 1.10-1.68 (44H, m), 2.66 (2H, ddd, J=10.6 Hz, 6.7 Hz, 3.6 Hz), 3.49 (2H, dd, J=9.6 Hz, 3.6 Hz), 3.55 (2H, t, J=9.6 Hz), 3.62 (2H, m), 4.02 (2H, t, J=9.6 Hz), 4.09 (2H, dd, J=12.1 Hz, 2.7 Hz), 4.18 (4H, m), 4.45 (4H, s), 4.52 (2H, d, J=10.6 Hz), 4.61 (2H, d, J=12.0 Hz), 4.67 (2H, d, J=12.0 Hz), 4.83 (2H, d, J=10.6 Hz), 4.84 (2H, d, J=11.0 Hz), 4.98 (2H, d, J=11.0 Hz), 5.10 (2H, d, J=3.6 Hz), 7.16-7.36 (40H, m)
$^{13}$C-NMR (75 MHz in CDCl$_3$) δ14.0, 14.1, 22.6 (2C), 24.9, 27.6, 27.8, 29.2, 29.3, 29.7, 31.1, 31.6, 31.8, 49.8, 62.2, 69.1, 71.9, 73.0, 75.2, 75.6, 77.8, 79.6, 80.2, 81.5, 93.8, 127.4, 127.5, 127.7, 127.8, 127.9, 128.2, 128.4 (3C), 137.8, 138.0, 138.6, 138.7, 174.3

Production Example E-6

Production of 6,6'-bis-O-[(2S,3S)-3-benzyloxy-2-hexyldecanoyl]-2,3,4,2',3',4'-hexabenzyl-α,α'-trehalose The target compound (166 mg, 62%) was obtained in the same manner as in Production Example E-1, except that the (2S,3S)-3-benzyloxy-2-hexyldecanoic acid (136 mg, 374 μmol) obtained in Production Example D-6 was used.
$[α]_D^{20}$ +50.1° (c 1.0)
FT-IR (neat) 3088, 3063, 3031, 2957, 2862, 1949, 1872, 1806, 1740 cm$^{-1}$
$^1$H-NMR (300 MHz in CDCl$_3$) δ0.84 (6H, t, J=7.0 Hz), 0.85 (6H, t, J=7.0 Hz), 1.10-1.68 (44H, m), 2.68 (2H, ddd, J=10.7 Hz, 6.7 Hz, 3.6 Hz), 3.50 (2H, dd, J=9.4 Hz, 3.4 Hz), 3.55 (2H, t, J=9.4 Hz), 3.62 (2H, m), 4.00 (2H, t, J=9.4 Hz), 4.06 (2H, m), 4.20 (4H, m), 4.43 (2H, d, J=11.8 Hz), 4.45 (2H, d, J=10.5 Hz), 4.48 (2H, d, J=11.8 Hz), 4.64 (2H, d, J=12.0 Hz), 4.70 (2H, d, J=12.0 Hz), 4.75 (2H, d, J=10.5 Hz), 4.83 (2H, d, J=10.9 Hz), 4.97 (2H, d, J=10.9 Hz), 5.09 (2H, d, J=3.4 Hz), 7.14-7.36 (40H, m)
$^{13}$C-NMR (75 MHz in CDCl$_3$) δ14.0, 22.5, 24.7, 27.6, 29.1, 29.2, 29.7, 30.9, 31.6, 31.7, 49.6, 62.1, 69.1, 71.8, 72.9, 75.1, 75.6, 77.7, 79.5, 80.0, 81.4, 93.9, 127.3, 127.5, 127.7 (2C), 127.8, 127.9, 128.1, 128.3, 128.4, 137.8, 137.9, 138.5, 138.6, 174.1

Production Example E-7

Production of 6,6'-bis-O-[(2R,3R)-3-methoxy-2-pentylnonanoyl]-2,3,4,2',3',4'-hexabenzyl-α,α'-trehalose The target compound (200 mg, 86%) was obtained in the same manner as in Production Example E-1, except that the (2R,3R)-3-methoxy-2-pentylnonanoic acid (101 mg, 391 μmol) obtained in Production Example D-9 was used.
$[α]_D^{20}$ +82.7° (c 0.5)
FT-IR (neat) 3088, 3063, 3031, 2929, 2858, 1950, 1874, 1807, 1738 cm$^{-1}$
$^1$H-NMR (300 MHz in CDCl$_3$) δ0.81 (6H, m), 0.87 (6H, m), 1.12-1.64 (36H, m), 2.58 (2H, ddd, J=10.5 Hz, 7.0 Hz, 3.6 Hz), 3.25 (6H, s), 3.34 (2H, dt, J=6.7 Hz, 3.6 Hz), 3.53 (2H, dd, J=9.6 Hz, 3.4 Hz), 3.56 (2H, t, J=9.6 Hz), 4.04 (2H, t, J=9.6 Hz), 4.19 (6H, m), 4.56 (2H, d, J=10.6 Hz), 4.67 (2H, d, J=12.0 Hz), 4.71 (2H, d, J=12.0 Hz), 4.86 (2H, d, J=10.9 Hz), 4.87 (2H, d, J=10.6 Hz), 5.00 (2H, d, J=10.9 Hz), 5.16 (2H, d, J=3.6 Hz), 7.23-7.37 (30H, m)
$^{13}$C-NMR (75 MHz in CDCl$_3$) δ14.0, 14.1, 22.4, 22.6, 24.7, 27.4, 27.6, 29.5, 30.5, 31.8, 49.5, 57.4, 62.2, 69.2, 73.0, 75.2, 75.7, 77.8, 79.5, 81.6, 81.9, 93.7, 127.5, 127.6, 127.7, 127.9 (2C), 128.0, 128.4 (2C), 137.8, 138.0, 138.7, 174.2
FABMS m/z (%) 1386 (5 M$^+$+Na), 673 (3))[x20], 475 (2) 181 (39), 91 (100)
HRMS (FAB$^+$) m/z Calculation Value: $C_{84}H_{114}O_{15}Na$ (M$^+$+Na) 1385.8055, Actual Measurement Value: 1385.8104

Production Example E-8

Production of 6,6'-bis-O-(2-butylhexanoyl)-2,3,4,2',3',4'-hexabenzyl-α,α'-trehalose A reaction and after treatment were performed in the same manner as in Production Example E-1 above. Specifically, 2-butylhexanoic acid (123 mg, 714 μmol) and a trehalose compound (2,3,4,2',3',4'-hexabenzyloxy-α,α'-trehalose) (300 mg, 340 μmol) were dissolved in anhydrous dichloromethane (3 ml); powdered molecular sieves 4A, 4-dimethylaminopyridine (20.7 mg, 170 μmol), and EDCI (163 mg, 848 μmol) were added sequentially thereto, and then the mixture was refluxed for two hours with heating. The reaction mixture was filtered using Celite 535. To the obtained filtrate was added distilled water to be extracted 3 times with dichloromethane. The resulting organic layer was dried with anhydrous magnesium sulfate, filtered, and condensed. The obtained residue was purified by column chromatography (silica gel: 15 g, n-hexane/ethyl acetate=7/1) to produce the target compound (358 mg, 88%).
$[α]_D^{20}$ +79.1° (c 1.1)
FT-IR (neat) 3088, 3063, 3031, 2956, 2860, 1950, 1874, 1807, 1739 cm$^{-1}$
$^1$H-NMR (300 MHz in CDCl$_3$) δ0.83 (12H, m), 1.23 (16H, m), 1.44 (4H, m), 1.58 (4H, m), 2.32 (2H, m), 3.54 (2H dd, J=9.5 Hz, 3.6 Hz), 3.56 (2H, t, J=9.5 Hz), 4.05 (2H, t, J=9.5 Hz), 4.09 (2H, m), 4.20 (4H, m), 4.54 (2H, d, J=10.6 Hz), 4.68 (2H, d, J=12.0 Hz), 4.72 (2H, d, J=12.0 Hz), 4.86 (2H, d, J=10.9 Hz), 4.88 (2H, d, J=10.6 Hz), 5.00 (2H, d, J=10.9 Hz), 5.18 (2H, d, J=3.6 Hz), 7.22-7.38 (30H, m)
$^{13}$C-NMR (75 MHz in CDCl$_3$) δ13.9 (2C), 22.6, 29.5 (2C), 32.1 (2C), 45.6, 62.0, 69.1, 73.0, 75.2, 75.6, 77.9, 79.5, 81.5, 93.6, 127.4, 127.6, 127.7, 127.8, 127.9, 128.4 (2C), 137.8, 138.0, 138.6, 176.1
FABMS m/z (%) 1214 (1 M$^+$+Na), 587 (2), 479 (4), 389 (9), 271 (3), 181 (39), 91 (100)
HRMS (FAB$^+$) m/z Calculation Value: $C_{74}H_{94}O_{13}Na$ (M$^+$+Na) 1213.6592, Actual Measurement Value: 1213.6562

Production Example E-9

Production of 6,6'-bis-O-(2-pentylheptanoyl)-2,3,4,2',3',4'-hexabenzyl-α,α'-trehalose The target compound (281 mg, 99%) was obtained in the same manner as in Production Example E-8, except that 2-pentylheptanoic acid (114 mg, 567 μmol) was used.

[α]$_D^{20}$ +69.8° (c 1.1)

FT-IR (neat) 3088, 3064, 3031, 2928, 2857, 1949, 1874, 1807, 1739 cm$^{-1}$ $^1$H-NMR (300 MHz in CDCl$_3$) δ0.81 (6H, t, J=6.3 Hz), 0.83 (6H, t, J=6.0 Hz), 1.20 (24H, m), 1.42 (4H, m), 1.55 (4H, m), 2.32 (2H, m), 3.54 (2H d, J=9.6 Hz), 3.55 (2H, t, J=9.6 Hz), 4.04 (2H, t, J=9.6 Hz), 4.11 (2H, m), 4.20 (4H, m), 4.53 (2H, d, J=10.9 Hz), 4.67 (2H, d, J=11.8 Hz), 4.71 (2H, d, J=11.8 Hz), 4.85 (2H, d, J=10.7 Hz), 4.87 (2H, d, J=10.9 Hz), 4.99 (2H, d, J=10.7 Hz), 5.17 (2H, d, J=3.3 Hz), 7.24-7.37 (30H, m)

$^{13}$C-NMR (75 MHz in CDCl$_3$) δ14.0 (2C), 22.5 (2C), 27.0, 27.1, 31.7, 32.3, 45.7, 62.0, 69.1, 73.0, 75.2, 75.7, 77.8, 79.6, 81.5, 93.7, 127.4, 127.6, 127.7, 127.8, 127.9 (2C), 128.4 (2C), 137.8, 138.0, 138.6, 176.1

FABMS m/z (%) 1270 (1 M$^+$+Na), 507 (10))$^{x10}$, 417 (5), 181 (35), 91 (100)

HRMS (FAB$^+$) m/z Calculation Value: C$_{78}$H$_{102}$O$_{13}$Na (M$^+$+Na) 1269.7218, Actual Measurement Value: 1269.7245

Production Example E-10

Production of 6,6'-bis-O-(2-hexyloctanoyl)-2,3,4,2',3',4'-hexabenzyl-α,α'-trehalose The target compound (261 mg, 89%) was obtained in the same manner as in Production Example E-8, except that 2-hexyloctanoic acid (109 mg, 476 μmol) was used.

[α]$_D^{20}$ +72.6° (c 1.2)

FT-IR (neat) 3088, 3064, 3031, 2929, 2857, 1948, 1869, 1804, 1739 cm$^{-1}$ $^1$H-NMR (300 MHz in CDCl$_3$) δ0.82 (6H, t, J=7.2 Hz), 0.85 (6H, t, J=6.6 Hz), 1.21 (32H, m), 1.43 (4H, m), 1.56 (4H, m), 2.32 (2H, m), 3.55 (2H dd, J=9.4 Hz, 3.6 Hz), 3.57 (2H, t, J=9.4 Hz), 4.05 (2H, t, J=9.4 Hz), 4.11 (2H, m), 4.19 (4H, m), 4.54 (2H, d, J=10.6 Hz), 4.67 (2H, d, J=11.8 Hz), 4.72 (2H, d, J=11.8 Hz), 4.85 (2H, d, J=10.9 Hz), 4.87 (2H, d, J=10.6 Hz), 4.99 (2H, d, J=10.9 Hz), 5.18 (2H, d, J=3.6 Hz), 7.23-7.37 (30H, m)

$^{13}$C-NMR (75 MHz in CDCl$_3$) δ14.0 (2C), 22.5, 27.3, 27.4, 29.2, 31.6 (2C), 32.3, 45.7, 62.0, 69.1, 73.0, 75.2, 75.6, 77.8, 79.7, 81.5, 93.6, 127.4, 127.6, 127.7, 127.8 (2C), 127.9, 128.3, 128.4 (2C), 137.8, 138.0, 138.6, 176.1

FABMS m/z (%) 1326 (1 M$^+$+Na), 643 (2), 535 (5), 445 (12), 271 (6), 181 (83), 91 (100)

HRMS (FAB$^+$) m/z Calculation Value: C$_{82}$H$_{110}$O$_{13}$Na (M$^+$+Na) 1325.7845, Actual Measurement Value: 1325.7819

Production Example E-11

Production of 6,6'-bis-O-(2-pentylnonanoyl)-2,3,4,2',3',4'-hexabenzyl-α,α'-trehalose The target compound (281 mg, 84%) was obtained in the same manner as in Production Example E-8, except that 2-pentylnonanoic acid (130 mg, 567 μmol) was used.

[α]$_D^{20}$ +66.9° (c 1.1)

FT-IR (neat) 3088, 3064, 3031, 2934, 2859, 1866, 1732 cm$^{-1}$ $^1$H-NMR (300 MHz in CDCl$_3$) δ0.84 (12H, m), 1.21 (32H, m), 1.41 (4H, m), 1.55 (4H, m), 2.32 (2H, m), 3.55 (2H dd, J=11.8 Hz, 3.6 Hz), 3.56 (2H, t, J=11.8 Hz), 4.05 (2H, t, J=11.8 Hz), 4.12 (2H, m), 4.20 (4H, m), 4.54 (2H, d, J=10.4 Hz), 4.67 (2H, d, J=12.1 Hz), 4.72 (2H, d, J=12.1 Hz), 4.86 (2H, d, J=10.7 Hz), 4.88 (2H, d, J=10.4 Hz), 5.00 (2H, d, J=10.7 Hz), 5.17 (2H, d, J=3.6 Hz), 7.22-7.38 (30H, m)

$^{13}$C-NMR (75 MHz in CDCl$_3$) δ14.0 (2C), 14.1 (2C), 22.4, 22.5, 22.6 (2C), 27.0, 27.1, 27.4 (2C), 29.1 (2C), 29.5, 31.7, 31.8, 32.3 (2C), 45.7 (2C), 62.0, 69.1, 73.0, 75.2, 75.7, 77.8, 79.6, 81.5, 93.7, 127.4, 127.6, 127.7, 127.8, 127.9 (2C), 128.4 (2C), 137.7, 138.0, 138.5, 176.1 (2C)

FABMS m/z (%) 1326 (2 M$^+$+Na), 643 (3), 535 (10))$^{x10}$, 445 (5), 181 (25), 91 (100)

HRMS (FAB$^+$) m/z Calculation Value: C$_{82}$H$_{110}$O$_{13}$Na (M$^+$+Na) 1325.7845, Actual Measurement Value: 1325.7891

Production Example E-12-1

Production of 6-O-[(2S,3S)-3-benzyloxy-2-butyloctanoyl]-2,3,4,2',3',4'-hexabenzyl-α,α'-trehalose The target compound of monoester (178 mg, 93%) was obtained in the same manner as in Production Example E-1, except that the (2S,3S)-3-benzyloxy-2-butyloctanoic acid (50.0 mg, 163 μmol) obtained in Production Example D-2 and a trehalose compound (2,3,4,2',3',4'-hexabenzyloxy-α,α'-trehalose) (287 mg, 327 μmol) were used.

[α]$_D^{20}$ +69.5° (c 1.0)

FT-IR (neat) 3499, 3088, 3063, 3031, 2955, 2869, 1951, 1873, 1809, 1739 cm$^{-1}$ $^1$H-NMR (300 MHz in CDCl$_3$) δ0.83 (6H, t, J=7.3 Hz), 1.10-1.62 (14H, m), 2.68 (1H, ddd, J=11.0 Hz, 7.2 Hz, 4.0 Hz), 3.52 (6H, m), 3.62 (1H, m), 4.04 (4H, m), 4.23 (2H, m), 4.44 (1H, m), 4.48 (2H, m), 4.66 (4H, m), 4.72 (1H, m), 4.78 (1H, d, J=10.3 Hz), 4.85 (1H, d, J=10.7 Hz), 4.87 (2H, d, J=9.8 Hz), 4.99 (2H, d, J=10.9 Hz), 5.07 (1H, d, J=3.6 Hz), 5.12 (1H, d, J=3.6 Hz), 7.16-7.38 (35H, m)

$^{13}$C-NMR (75 MHz in CDCl$_3$) δ14.3, 14.4, 22.9, 23.0, 24.8, 27.7, 30.2, 31.3, 32.3, 50.0, 53.8, 61.8, 62.5, 69.5, 71.6, 72.2, 73.2, 73.4, 75.4, 75.6, 75.9, 76.0, 77.7, 78.1, 79.8, 80.4, 81.9, 94.1, 94.2, 127.7, 127.8 (2C), 127.9 (3C), 128.0, 128.1, 128.2 (2C), 128.3, 128.4, 128.6, 128.7 (2C), 128.8, 138.2, 138.3 (2C), 138.5, 138.9, 139.0, 139.1, 174.5

FABMS m/z (%) 1194 (6 M$^+$+Na))$^{x8}$, 271 (10), 181 (100), 107 (15), 91 (100)

HRMS (FAB$^+$) m/z Calculation Value: C$_{73}$H$_{86}$O$_{13}$Na (M$^+$+Na) 1193.5966, Actual Measurement Value: 1193.5962

Production Example E-12-2

Production of 6-O-[(2R,3R)-3-benzyloxy-2-butyloctanoyl]-6'-O-[(2S,3S)-3-benzyloxy-2-butyloctanoyl]-2,3,4,2',3',4'-hexabenzyl-α,α'-trehalose The target compound (141 mg, 99%) was obtained in the same manner as in Production Example E-1, except that the 6-O-[(2S,3S)-3-benzyloxy-2-butyloctanoyl]-2,3,4,2',3',4'-hexabenzyl-α,α'-trehalose (115 mg, 98.0 μmol) obtained in Production Example E-12-1 and the (2R,3R)-3-benzyloxy-2-butyloctanoic acid (36.1 mg, 118 μmol) obtained in Production Example D-1 were used.

[α]$_D^{20}$ +47.5° (c 2.2)

FT-IR (neat) 3088, 3063, 3031, 2954, 2861, 1950, 1874, 1808, 1739 cm$^{-1}$ $^1$H-NMR (300 MHz in CDCl$_3$) δ0.84 (12H, m), 1.10-1.68 (28H, m), 2.67 (2H, m), 3.49 (2H, m), 3.55 (2H, m), 3.62 (2H, m), 4.01 (2H, m), 4.07 (2H, m), 4.22 (4H, m), 4.44 (1H, m), 4.46 (4H, s), 4.53 (1H, d, J=10.6 Hz), 4.62 (1H, d, J=11.8 Hz), 4.64 (1H, d, J=10.9 Hz), 4.68 (1H, d, J=10.9 Hz), 4.70 (1H, d, J=11.8 Hz), 4.76 (1H, d, J=10.5 Hz), 4.84 (3H, m), 4.98 (1H, d, J=10.9 Hz), 4.99 (1H, d, J=10.9 Hz), 5.08 (1H, d, J=3.6 Hz), 5.11 (1H, d, J=3.4 Hz), 7.17-7.38 (40H, m)

¹³C-NMR (75 MHz in CDCl₃) δ14.2, 14.3 (2C), 14.4, 22.9 (2C), 23.0, 24.8, 24.9, 27.6, 30.1, 30.3, 31.2, 31.3, 32.2, 32.3, 49.9, 50.0, 62.4, 62.5, 69.4, 72.1, 73.2, 73.3, 75.5, 76.0 (2C), 78.0, 78.1, 79.7, 79.9, 80.3, 80.5, 81.8, 94.2, 127.7, 127.8, 127.9 (2C), 128.0, 128.1, 128.2, 128.3, 128.5, 128.7 (2C), 128.8, 138.1, 138.3, 138.8, 138.9, 139.0, 174.5, 174.6

FABMS m/z (%) 1482 (3 M⁺+Na), 721 (2), 613 (10), 523 (12), 325 (12))$^{x50}$, 91 (100)

HRMS (FAB⁺) m/z Calculation Value: $C_{92}H_{114}O_{15}Na$ (M⁺+Na) 1481.8055, Actual Measurement Value: 1481.8077

Production-Example E-13-1

Production of 6-O-[(2R,3R)-3-benzyloxy-2-pentyl-nonanoyl]-2,3,4,2',3',4'-hexabenzyl-α,α'-trehalose The target compound of monoester (162 mg, 83%) was obtained in the same manner as in Production Example E-1, except that the (2R,3R)-3-benzyloxy-2-pentylnonanoic acid (54.4 mg, 163 μmol) obtained in Production Example D-3 and a trehalose compound (2,3,4,2',3',4'-hexabenzyloxy-α,α'-trehalose) (287 mg, 327 μmol) were used.

$[α]_D^{20}$ +55.3° (c 5.0)

FT-R (neat) 3500, 3088, 3063, 3031, 2928, 2859, 1950, 1872, 1808, 1736 cm⁻¹

¹H-NMR (300 MHz in CDCl₃) δ0.85 (6H, m), 1.10-1.72 (18H, m), 2.66 (1H, ddd, J=10.7 Hz, 6.9 Hz, 3.3 Hz), 3.55 (6H, m), 3.61 (1H, m), 4.13 (6H, m), 4.46 (2H, s), 4.53 (1H, d, J=11.8 Hz), 4.65 (4H, m), 4.71 (1H, d, J=11.8 Hz), 4.85 (2H, d, J=11.0 Hz), 4.87 (2H, d, J=10.2 Hz), 4.99 (1H, d, J=10.7 Hz), 5.00 (1H, d, J=11.0 Hz), 5.08 (1H, d, J=3.8 Hz), 5.14 (1H, d, J=3.6 Hz), 7.17-7.42 (35H, m)

¹³C-NMR (50 MHz in CDCl₃) δ14.0, 14.1, 22.5, 22.6, 24.9, 27.5, 29.4, 31.1, 31.8, 49.8, 61.6, 62.2, 69.1, 71.2, 71.9, 72.9, 73.0, 75.0, 75.2, 75.6, 75.7, 77.2, 77.3, 77.8, 79.4, 79.6, 80.3, 81.6, 93.7, 94.0, 127.4, 127.6, 127.8, 127.9 (2C), 128.1, 128.2, 128.4 (2C), 128.5, 137.8, 138.0, 138.2, 138.6, 138.7, 138.8, 174.4

FABMS m/z (%) 1222 (5 M⁺+Na), 641 (6), 551 (5), 443 (3), 317 (12), 181 (100), 92 (100), 91 (100)

HRMS (FAB⁺) m/z Calculation Value: $C_{75}H_{90}O_{13}Na$ (M⁺+Na) 1221.6279, Actual Measurement Value: 1221.6251

Production-Example E-13-2

Production of 6-O-[(2R,3R)-3-benzyloxy-2-pentyl-nonanoyl]-6'-O-[(2S,3S)-3-benzyloxy-2-pentyl-nonanoyl]-2,3,4,2',3',4'-hexabenzyl-α,α'-trehalose The target compound (124 mg, 91%) was obtained in the same manner as in Production Example E-1, except that the 6-O-[(2R,3R)-3-benzyloxy-2-pentylnonanoyl]-2,3,4,2',3',4'-hexabenzyl-α,α'-trehalose (108 mg, 90.0 μmol) obtained in Production Example E-13-1 and the (2S,3S)-3-benzyloxy-2-pentylnonanoic acid (31.7 mg, 95.0 μmol) obtained in Production Example D-4 were used.

$[α]_D^{20}$ +68.6° (c 0.6)

FT-IR (neat) 3088, 3063, 3031, 2929, 2859, 1949, 1871, 1807, 1738 cm⁻¹

¹H-NMR (300 MHz in CDCl₃) δ0.84 (12H, m), 1.10-1.72 (36H, m), 2.66 (1H, m), 2.69 (1H, m), 3.48 (1H, dd, J=9.3 Hz, 5.8 Hz), 3.51 (1H, m), 3.55 (2H, m), 3.61 (1H, m), 3.62 (1H, m), 4.01 (2H, m), 4.07 (2H, m), 4.18 (2H, m), 4.21 (2H, m), 4.44 (1H, m), 4.46 (4H, s), 4.52 (1H, d, J=10.7 Hz), 4.61 (1H, d, J=11.8 Hz), 4.66 (2H, s), 4.69 (1H, d, J=11.8 Hz), 4.75 (1H, d, J=10.7 Hz), 4.84 (3H, m), 4.98 (1H, d, J=10.7 Hz), 4.99 (1H, d, J=11.0 Hz), 5.08 (1H, d, J=3.6 Hz), 5.11 (1H, d, J=3.6 Hz), 7.16-7.38 (40H, m)

¹³C-NMR (75 MHz in CDCl₃) δ14.1, 22.4, 22.5, 22.6, 24.8, 24.9, 27.4, 27.5, 29.4, 29.5, 31.1, 31.8, 49.6, 49.8, 62.2, 69.1, 71.8, 72.9, 73.0, 75.3, 75.7, 79.5, 79.6, 80.0, 80.2, 81.5, 94.0, 127.4, 127.5, 127.6 (2C), 127.8, 127.9, 128.0, 128.3, 128.4, 128.5, 137.8, 138.0, 138.5, 138.6, 138.7, 174.2, 174.3

FABMS m/z (%) 1539 (3 M⁺+1+Na), 551 (8), 443 (7), 271 (35)))$^{65}$, 181 (29), 91 (100)

HRMS (FAB⁺) m/z Calculation Value: $C_{96}H_{123}O_{15}Na$ (M⁺+1+Na) 1538.8760, Actual Measurement Value: 1538.8756

Production-Example E-14-1

Production of 6-O-[(2S,3S)-3-benzyloxy-2-hexylde-canoyl]-2,3,2',3',4'-hexabenzyl-α,α'-trehalose The target compound of monoester (114 mg, 81%) was obtained in the same manner as in Production Example E-1, except that the (2S,3S)-3-benzyloxy-2-hexyldecanoic acid (40.0 mg, 115 μmol) obtained in Production Example D-6 and a trehalose compound (2,3,4,2',3',4'-hexabenzyloxy-α,α'-trehalose (102 mg, 116 μmol) were used.

$[α]_D^{20}$ +66.9° (c 1.0)

FT-IR (neat) 3504, 3088, 3063, 3031, 2926, 2857, 1956, 1878, 1800, 1736 cm⁻¹

¹H-NMR (300 MHz in CDCl₃) δ0.83 (3H, t, J=7.1 Hz), 0.86 (3H, t, J=6.6 Hz), 1.12-1.68 (22H, m), 2.68 (1H, ddd, J=10.7 Hz, 6.9 Hz, 3.3 Hz), 3.53 (6H, m), 3.62 (1H, m), 4.03 (4H, m), 4.23 (2H, m), 4.45 (1H, m), 4.47 (2H, m), 4.67 (4H, m), 4.71 (1H, m), 4.78 (1H, d, J=10.4 Hz), 4.85 (2H, d, J=10.7 Hz), 9.86 (2H, d, J=10.4 Hz), 4.98 (2H, d, J=11.0 Hz), 5.07 (1H, d, J=3.6 Hz), 5.12 (1H, d, J=3.6 Hz), 7.16-7.38 (35H, m)

¹³C-NMR (75 MHz in CDCl₃) δ14.0, 19.1, 22.6 (2C), 24.7, 27.6, 29.2, 29.3, 29.7, 30.9, 31.6, 31.7, 49.7, 61.5, 62.1, 69.1, 71.1, 71.8, 72.8, 73.0, 75.0, 75.2, 75.5, 75.7, 77.3, 77.8, 79.4, 79.5, 80.0, 81.5, 93.7, 93.9, 127.3, 127.4, 127.5 (2C), 127.6, 127.7, 127.8, 127.9, 128.0, 128.1, 128.3, 128.4, 137.8, 137.9 (2C), 138.1, 138.5, 138.6, 138.7, 174.1

FABMS m/z (%) 1250 (1 M⁺+Na), 669 (1), 471 (1), 345 (3), 91 (100)

HRMS (FAB⁺) m/z Calculation Value: $C_{77}H_{94}O_{13}Na$ (M⁺+Na) 1249.6592, Actual Measurement Value: 1249.6595

Production Example E-14-2

Production of 6-O-[(2R,3R)-3-benzyloxy-2-hexylde-canoyl]-6'-O-[(2S,3S)-3-benzyloxy-2-hexylde-canoyl]-2,3,4,2',3',4'-hexabenzyl-α,α'-trehalose The target compound (111 mg, 81%) was obtained in the same manner as in Production Example E-1, except that the 6-O-[(2S,3S)-3-benzyloxy-2-hexyldecanoyl]-2,3,4,2',3',4'-hexabenzyl-α,α'-trehalose (107 mg, 87.2 μmol) obtained in Production Example E-14-1 and the (2R,3R)-3-benzyloxy-2-hexyldecanoic acid (33.3 mg, 95.5 μmol) obtained in Production Example D-5 were used.

$[α]_D^{20}$ +63.7° (c 1.2)

FT-IR (neat) 3088, 3063, 3031, 2927, 2856, 1948, 1869, 1807, 1737 cm⁻¹

¹H-NMR (300 MHz in CDCl₃) δ0.84 (12H, m), 1.10-1.72 (44H, m), 2.66 (1H, m), 2.69 (1H, m), 3.48 (1H, dd, J=8.9 Hz, 3.6 Hz), 3.51 (1H, m), 3.55 (2H, t, J=9.8 Hz), 3.61 (1H, m), 3.62 (1H, m), 4.01 (2H, t, J=9.8 Hz), 4.09 (2H, m), 4.18 (2H, m), 4.21 (2H, m), 4.44 (1H, m), 4.46 (4H, s), 4.52 (1H, d,

J=10.9 Hz), 4.61 (1H, d, J=11.7 Hz), 4.66 (2H, s), 4.70 (1H, d, J=11.7 Hz), 4.75 (1H, d, J=10.6 Hz), 4.83 (3H, m), 4.97 (1H, d, J=10.9 Hz), 4.98 (1H, d, J=11.0 Hz), 5.08 (1H, d, J=3.5 Hz), 5.11 (1H, d, J=3.5 Hz), 7.16-7.36 (40H, m)

$^{13}$C-NMR (75 MHz in CDCl$_3$) δ14.0, 22.5, 24.7, 24.8, 27.6, 27.7, 29.2 (2C), 29.6, 29.7, 30.9, 31.0, 31.5, 31.6, 31.7, 49.6, 49.7, 62.1, 62.2, 69.1, 71.8, 72.9 (2C), 75.1, 75.5, 75.6, 77.7, 79.5, 79.6, 79.9, 80.2, 81.4, 93.8, 127.3 (3C), 127.5, 127.6, 127.7, 127.8 (2C), 128.1, 128.3, 128.4, 137.8, 137.9, 138.5, 138.6 (2C), 174.1, 174.2

Production Example E-15

Production of 6,6'-bis-N-[(2R,3R)-3-benzyloxy-2-pentylnonanoylamino]-6,6'-dideoxy-2,3,4,2',3',4'-hexabenzyl-α,α'-trehalose The target compound (254 mg, 81%) was obtained in the same manner as in Production Example E-1, except that the (2R,3R)-3-benzyloxy-2-pentylnonanoic acid (159 mg, 476 μmol) obtained in Production Example D-3 and a diamine (6,6'-diamino-6,6'-dideoxy-2,3,4,2',3',4'-hexabenzyloxy-α,α'-trehalose) (182 mg, 207 μmol) were used.

$[α]_D^{20}$ +59.5° (c 0.4)

FT-IR (neat) 3386, 3087, 3063, 3031, 2928, 2858, 1950, 1873, 1807, 1726, 1672 cm$^{-1}$ $^1$H-NMR (300 MHz in CDCl$_3$) δ0.84 (12H, m), 1.08-1.76 (36H, m), 2.29 (2H, dt, J=9.6 Hz, 5.2 Hz), 2.93 (2H, m), 3.30 (2H, dd, J=9.8 Hz, 3.3 Hz), 3.31 (2H, t, J=9.8 Hz), 3.55 (2H, q, J=5.8 Hz), 3.97 (2H, t, J=9.8 Hz), 4.06 (4H, m), 4.44 (2H, d, J=11.1 Hz), 4.52 (2H, d, J=12.1 Hz), 4.56 (2H, d, J=11.1 Hz), 4.58 (2H, d, J=12.1 Hz), 4.60 (2H, d, J=9.9 Hz), 4.75 (2H, d, J=9.9 Hz), 4.85 (2H, d, J=11.1 Hz), 4.90 (2H, d, J=3.6 Hz), 4.94 (2H, d, J=11.1 Hz), 6.36 (NH, br d, J=7.5 Hz), 7.20-7.38 (40H, m)

$^{13}$C-NMR (75 MHz in CDCl$_3$) δ14.1, 22.5, 22.6, 25.2, 27.4, 29.5, 29.9, 31.8 (2C), 32.4, 38.5, 52.4, 69.5, 72.9 (2C), 75.4, 77.2, 78.4, 79.3, 80.5, 81.3, 93.8, 127.3, 127.4, 127.7, 127.8, 128.3 (2C), 128.4, 128.5, 137.9, 138.1, 138.5, 138.8, 174.3

FABMS m/z (%) 1537 (3 M$^+$+1+Na), 1406 (11))$^{x15}$, 749 (2), 641 (7), 181 (24), 91 (100)

HRMS (FAB$^+$) m/z Calculation Value: C$_{96}$H$_{124}$O$_{13}$N$_2$Na (M$^+$+Na) 1535.9001, Actual Measurement Value: 1535.9033

Production Example E-16

Production of 6,6'-bis-N-[(2R,3R)-3-methoxy-2-pentylnonanoylamino]-6,6'-dideoxy-2,3,4,2',3',4'-hexabenzyl-α,α'-trehalose The target compound (228 mg, 80%) was obtained in the same manner as in Production Example E-1, except that the (2R,3R)-3-methoxy-2-pentylnonanoic acid (120 mg, 464 μmol) obtained in Production Example D-9 and the diamine (184 mg, 209 μmol) used in Production Example E-15 were used.

$[α]_D^{20}$ +30.7° (c 0.5)

FT-IR (neat) 3429, 3380, 3088, 3063, 3031, 2935, 2858, 1950, 1873, 1808, 1673 cm$^{-1}$ $^1$H-NMR (300 MHz in CDCl$_3$) δ0.85 (12H, m), 1.16-1.69 (36H, m), 2.22 (2H, dt, J=9.9 Hz, 5.5 Hz), 3.07 (2H, m), 3.25 (2H, m), 3.30 (6H, s), 3.35 (2H, t, J=9.6 Hz), 3.46 (2H, dd, J=9.6 Hz, 3.6 Hz), 3.96 (2H, m), 4.04 (2H, t, J=9.3 Hz), 4.12 (2H, m), 4.64 (4H, d, J=10.7 Hz), 4.70 (2H, d, J=10.7 Hz), 4.80 (2H, d, J=10.7 Hz), 4.88 (2H, d, J=11.0 Hz), 4.97 (2H, d, J=11.0 Hz), 5.11 (2H, d, J=3.3 Hz), 6.24 (NH, br d, J=6.0 Hz), 7.20-7.38 (30H, m)

$^{13}$C-NMR (75 MHz in CDCl$_3$) δ14.0, 22.5 (2C), 25.0, 27.3, 29.5, 29.8, 31.7 (2C), 31.8, 38.7, 52.1, 58.4, 69.6, 73.0, 75.4 (2C), 78.5, 79.2, 81.3, 82.0, 93.5, 127.4, 127.5, 127.7 (2C), 128.3, 128.4 (2C), 137.8, 138.1, 138.8, 174.2

FABMS m/z (%) 1384 (15 M$^+$+Na), 1362 (7 M$^+$+1))$^{x15}$, 672 (5), 564 (9), 181 (7), 91 (100)

HRMS (FAB$^+$) m/z Calculation Value: C$_{84}$H$_{117}$O$_{13}$N$_2$ (M$^+$+1) 1361.8556, Actual Measurement Value: 1361.8560

Production Example E-17

Production of 6,6'-bis-N-(2-hexyloctanoylamino)-6,6'-dideoxy-2,3,4,2',3',4'-hexabenzyl-α,α'-trehalose The target compound (248 mg, 84%) was obtained in the same manner as in Production Example E-1, except that 2-hexyloctanoic acid (109 mg, 477 μmol) and the diamine (200 mg, 227 μmol) used in Production Example E-15 were used.

$[α]_D^{20}$ +44.9° (c 1.1)

FT-IR (neat) 3426, 3339, 3088, 3063, 3031, 2927, 2855, 1949, 1873, 1807, 1677 cm$^{-1}$ $^1$H-NMR (300 MHz in CDCl$_3$) δ0.85 (12H, m), 1.23 (32H, m), 1.36 (4H, m), 1.53 (4H, m), 1.84 (2H, m), 3.00 (2H, m), 3.30 (2H t, J=9.6 Hz), 3.47 (2H, dd, J=9.6 Hz, 3.5 Hz), 3.93 (2H, m), 4.05 (2H, t, J=9.6 Hz), 4.12 (2H, m), 4.63 (4H, m), 4.74 (2H, d, J=12.0 Hz), 4.81 (2H, d, J=10.2 Hz), 4.89 (2H, d, J=11.0 Hz), 4.98 (2H, d, J=11.0 Hz), 5.08 (2H, d, J=3.5 Hz), 5.30 (NH, br d, J=6.1 Hz), 7.22-7.40 (30H, m)

$^{13}$C-NMR (75 MHz in CDCl$_3$) δ14.0, 22.5, 27.6, 27.7, 29.3 (2C), 31.7, 32.8, 33.0, 38.5, 48.2, 69.6, 73.1, 75.2, 75.5, 78.3, 79.4, 81.5, 93.9, 127.2, 127.5, 127.7, 127.8, 128.3, 128.4, 128.5, 137.8, 138.0, 138.5, 175.8

FABMS m/z (%) 1302 (4 M$^+$+1), 1194 (2), 642 (25), 534 (60), 432 (12), 282 (10), 181 (42), 91 (100)

HRMS (FAB$^+$) m/z Calculation Value: C$_{82}$H$_{113}$O$_{11}$N$_2$ (M$^+$+1) 1301.8345, Actual Measurement Value: 1301.8300

Production Example E-18

Production of 6,6'-bis-N-(2-pentylnonanoylamino)-6,6'-dideoxy-2,3,4,2',3',4'-hexabenzyl-α,α'-trehalose The target compound (299 mg, 90%) was obtained in the same manner as in Production Example E-1, except that 2-pentylnonanoic acid (130 mg, 569 μmol) and the diamine (224 mg, 255 μmol) used in Production Example E-15 were used.

$[α]_D^{20}$ +34.6° (c 0.7)

FT-IR (neat) 3426, 3334, 3088, 3063, 3031, 2938, 2857, 1949, 1870, 1807, 1681 cm$^{-1}$ $^1$H-NMR (300 MHz in CDCl$_3$) δ0.86 (12H, m), 1.23 (36H, m), 1.54 (4H, m), 1.84 (2H, m), 2.99 (2H, m), 3.30 (2H t, J=9.6 Hz), 3.47 (2H, dd, J=9.6 Hz, 3.6 Hz), 3.94 (2H, m), 4.04 (2H, t, J=9.6 Hz), 4.11 (2H, m), 4.63 (4H, m), 4.73 (2H, d, J=12.1 Hz), 4.81 (2H, d, J=9.9 Hz), 4.90 (2H, d, J=11.0 Hz), 4.98 (2H, d, J=11.0 Hz), 5.08 (2H, d, J=3.6 Hz), 5.29 (NH, br d, J=8.5 Hz), 7.22-7.42 (30H, m)

$^{13}$C-NMR (75 MHz in CDCl$_3$) δ14.0, 22.5, 22.6, 27.3, 27.5, 27.7, 27.8, 29.2 (2C), 29.6 (2C), 31.8 (2C), 32.8, 32.9, 33.0, 38.5, 48.2, 69.6, 73.1, 75.3, 75.5 (2C), 78.3, 79.4, 81.5, 93.9, 127.3, 127.5, 127.7 (2C), 127.9, 128.3, 128.4, 128.5, 137.8, 138.0, 138.6, 175.9

FABMS m/z (%) 1302 (2 M$^+$+1), 1194 (2))$^{x15}$, 642 (3), 534 (6), 181 (5), 91 (100)
HRMS (FAB$^+$) m/z Calculation Value: $C_{82}H_{113}O_{11}N_2$ (M$^+$+1) 1301.8344, Actual Measurement Value: 1301.8363

Production Example F-1

Production of 6,6'-bis-O-[(2R,3R)-3-hydroxy-2-pentylnonanoyl]-α,α'-trehalose

The 6,6'-bis-O-[(2R,3R)-3-benzyloxy-2-pentylnonanoyl]-2,3,4,2',3',4'-hexabenzyl-α,α'-trehalose (150 mg, 99.0 μmol) obtained in Production Example E-1 was dissolved in a mixture solution (3 ml) having a ratio of chloroform:methanol:acetic acid=1:1:0.1; palladium hydroxide (20 w/w %, 30.0 mg, 42.9 μmol) was added thereto, and then the mixture was stirred for 6 hours under 1 atm of hydrogen. The reaction mixture was condensed, and the obtained residue was purified by column chromatography (silica gel: 4 g, dichloromethane:methanol=9:2) to produce the target compound (66.3 mg, 84%).
$[α]_D^{20}$ +103.9° (c 3.3 MeOH)
FT-IR (neat) 3390, 2932, 2858, 1731 cm$^{-1}$
$^1$H-NMR (300 MHz in CD$_3$OD) δ0.85 (12H, m), 1.14-1.68 (36H, m), 2.39 (2H, ddd, J=11.3 Hz, 7.2 Hz, 4.4 Hz), 3.29 (2H, m), 3.42 (2H, dd, J=9.8 Hz, 3.7 Hz), 3.64 (2H, m), 3.74 (2H, t, J=9.8 Hz), 4.02 (2H, ddd, J=10.0 Hz, 5.2 Hz, 1.9 Hz), 4.14 (2H, dd, J=12.0 Hz, 5.2 Hz), 4.38 (2H, dd, J=12.0 Hz, 1.9 Hz), 5.00 (2H, d, J=3.7 Hz)
$^{13}$C-NMR (75 MHz in CD$_3$OD) δ14.4, 14.5, 23.5, 23.7, 26.6, 28.3, 29.8, 30.4, 32.9, 33.0, 35.6, 54.2, 64.4, 71.4, 72.0, 73.1, 73.6, 74.3, 95.4, 176.1
FABMS m/z (%) 818 (100), 817 (5 M$^+$+Na), 816 (8), 591 (6), 573 (5), 429 (10), 227 (18), 55 (60)
HRMS (FAB$^+$) m/z Calculation Value: $C_{40}H_{74}O_{15}Na$ (M$^+$+Na) 817.4926, Actual Measurement Value: 817.4948

Production Example F-2

Production of 6,6'-bis-O-[(2S,3S)-3-hydroxy-2-pentylnonanoyl]-α,α'-trehalose

The target compound (58.0 mg, 79%) was obtained in the same manner as in Production Example F-1, except that the 6,6'-bis-O-[(2S,3S)-3-benzyloxy-2-pentylnonanoyl]-2,3,4,2',3',4'-hexabenzyl-α,α'-trehalose (140 mg, 92.4 μmol) obtained in Production Example E-2 was used.
$[α]_D^{20}$ +74.0° (c 2.9 MeOH)
FT-IR (neat) 3418, 2956, 2859, 1732 cm$^{-1}$
$^1$H-NMR (300 MHz in CD$_3$OD) δ0.86 (12H, m), 1.14-1.68 (36H, m), 2.39 (2H, ddd, J=10.3 Hz, 7.4 Hz, 4.3 Hz), 3.30 (2H, dd, J=10.0 Hz, 9.8 Hz), 3.43 (2H, dd, J=9.8 Hz, 3.7 Hz), 3.64 (2H, m), 3.74 (2H, t, J=9.8 Hz), 3.99 (2H, ddd, J=10.0 Hz, 5.2 Hz, 1.9 Hz), 4.15 (2H, dd, J=11.8 Hz, 5.2 Hz), 4.39 (2H, dd, J=11.8 Hz, 1.9 Hz), 5.01 (2H, d, J=3.7 Hz)
$^{13}$C-NMR (75 MHz in CD$_3$OD) δ14.4, 14.5, 23.5, 23.7, 26.5, 28.3, 29.8, 30.4, 32.9, 33.0, 35.6, 54.2, 64.3, 71.5, 71.9, 73.1, 73.5, 74.4, 95.3, 176.2
FABMS m/z (%) 818 (100), 817 (5 M$^+$+Na), 816 (10), 591 (5), 573 (4), 429 (6), 411 (5), 227 (11), 55 (44)
HRMS (FAB$^+$) m/z Calculation Value: $C_{40}H_{74}O_{15}Na$ (M$^+$+Na) 817.4926, Actual Measurement Value: 817.4948

Production Example F-3

Production of 6,6'-bis-O-[(2R,3S)-3-hydroxy-2-pentylnonanoyl]-α,α'-trehalose

The target compound (69.3 mg, 88%) was obtained in the same manner as in Production Example F-1, except that the 6,6'-bis-O-[(2R,3S)-3-benzyloxy-2-pentylnonanoyl]-2,3,4,2',3',4'-hexabenzyl-α,α'-trehalose (150 mg, 99.0 μmol) obtained in Production Example E-3 was used.
$[α]_D^{20}$ +86.5° (c 3.3 MeOH)
FT-IR (neat) 3373, 2954, 2929, 2858, 1732 cm$^{-1}$
$^1$H-NMR (300 MHz in CD$_3$OD) δ0.85 (12H, m), 1.12-1.72 (36H, m), 2.34 (2H, ddd, J=10.2 Hz, 7.3 Hz, 4.0 Hz), 3.28 (2H, dd, J=9.8 Hz, 8.9 Hz), 3.42 (2H, dd, J=9.8 Hz, 3.7 Hz), 3.60 (2H, dt, J=7.8 Hz, 3.7 Hz), 3.74 (2H, t, J=9.2 Hz), 3.99 (2H, ddd, J=10.0 Hz, 5.2 Hz, 1.8 Hz), 4.13 (2H, dd, J=12.0 Hz, 5.2 Hz), 4.38 (2H, dd, J=12.0 Hz, 1.8 Hz), 5.00 (2H, d, J=3.7 Hz)
$^{13}$C-NMR (75 MHz in CD$_3$OD) δ14.4, 14.5, 23.5, 23.7, 26.9, 28.4, 29.3, 30.3, 33.0 (2C), 36.2, 54.2, 64.4, 71.4, 72.0, 73.1, 73.3, 74.5, 95.3, 176.3
FABMS m/z (%) 818 (100), 817 (5 M$^+$+Na), 816 (12), 591 (6), 573 (4), 429 (6), 227 (15), 55 (46)
HRMS (FAB$^+$) m/z Calculation Value: $C_{40}H_{74}O_{15}Na$ (M$^+$+Na) 817.4925, Actual Measurement Value: 817.4919

Production Example F-4

Production of 6,6'-bis-O-[(2S,3R)-3-hydroxy-2-pentylnonanoyl]-α,α'-trehalose

The target compound (70.1 mg, 89%) was obtained in the same manner as in Production Example F-1, except that the 6,6'-bis-O-[(2S,3R)-3-benzyloxy-2-pentylnonanoyl]-2,3,4,2',3',4'-hexabenzyl-α,α'-trehalose (150 mg, 99.0 μmol) obtained in Production Example E-4 was used.
$[α]_D^{20}$ +87.3° (c 3.3 MeOH)
FT-IR (neat) 3389, 2955, 2930, 2859, 1731 cm$^{-1}$
$^1$H-NMR (300 MHz in CD$_3$OD) δ0.85 (12H, m), 1.12-1.74 (36H, m), 2.34 (2H, ddd, J=10.3 Hz, 7.6 Hz, 4.0 Hz), 3.31 (2H, dd, J=10.0 Hz, 8.8 Hz), 3.42 (2H, dd, J=9.8 Hz, 3.7 Hz), 3.59 (2H, dt, J=7.8 Hz, 2.9 Hz), 3.74 (2H, t, J=8.9 Hz), 3.99 (2H, ddd, J=10.0 Hz, 4.8 Hz, 2.1 Hz), 4.17 (2H, dd, J=12.0 Hz, 4.8 Hz), 4.33 (2H, dd, J=12.0 Hz, 2.1 Hz), 5.00 (2H, d, J=3.7 Hz)
$^{13}$C-NMR (75 MHz in CD$_3$OD) δ14.4, 14.5, 23.5, 23.7, 26.9, 28.4, 29.5, 30.3, 32.9, 33.0, 36.1, 54.3, 64.2, 71.4, 71.8, 73.1, 73.3, 74.5, 95.4, 176.3
FABMS m/z (%) 818 (100), 817 (5 M$^+$+Na), 816 (11), 591 (6), 573 (5), 429 (7), 411 (4), 227 (10), 55 (41)
HRMS (FAB$^+$) m/z Calculation Value: $C_{40}H_{74}O_{15}Na$ (M$^+$+Na) 817.4925, Actual Measurement Value: 817.4919

Production Example F-5

Production of 6,6'-bis-O-[(2R,3R)-2-hexyl-3-hydroxydecanoyl]-α,α'-trehalose

The target compound (66.6 mg, 82%) was obtained in the same manner as in Production Example F-1, except that 6,6'-bis-O-[(2R,3R)-3-benzyloxy 2-hexyldecanoyl]-2,3,4,2',3',4'-hexabenzyl-α,α'-trehalose (150 mg, 95.5 μmol) obtained in Production Example E-5 was used.
$[α]_D^{20}$ +97.2° (c 2.1 MeOH)
FT-IR (neat) 3379, 2927, 2857, 1731 cm$^{-1}$
$^1$H-NMR (300 MHz in CD$_3$OD) δ0.85 (6H, t, J=6.1 Hz), 0.87 (6H, t, J=5.2 Hz), 1.16-1.63 (44H, m), 2.39 (2H, ddd, J=10.3 Hz, 6.1 Hz, 3.2 Hz), 3.29 (2H, m), 3.42 (2H, dd, J=9.8 Hz, 3.7 Hz), 3.63 (2H, m), 3.74 (2H, t, J=9.8 Hz), 4.02 (2H, ddd, J=9.8 Hz, 5.4 Hz, 2.2 Hz), 4.14 (2H, dd, J=11.8 Hz, 5.4 Hz), 4.38 (2H, dd, J=11.8 Hz, 2.2 Hz), 5.00 (2H, d, J=3.7 Hz)

$^{13}$C-NMR (75 MHz in CD$_3$OD) δ14.5, 23.7 (2C), 26.7, 28.6, 29.8, 30.3, 30.4, 30.6, 32.8, 33.0, 35.6, 54.2, 64.5, 71.4, 72.0, 73.1, 73.6, 74.4, 95.4, 176.2

FABMS m/z (%) 874 (40 M$^+$+Na), 485 (8), 255 (20), 215 (10), 165 (15), 154 (45), 69 (90), 55 (100)

HRMS (FAB$^+$) m/z Calculation Value: C$_{44}$H$_{82}$O$_{15}$Na (M$^+$+Na) 873.5551, Actual Measurement Value: 873.5533

Production Example F-6

Production of 6,6'-bis-O-[(2S,3S)-2-hexyl-3-hydroxydecanoyl]-α,α'-trehalose

The target compound (69.9 mg, 86%) was obtained in the same manner as in Production Example F-1, except that the 6,6'-bis-O-[(2S,3S)-3-benzyloxy-2-hexyldecanoyl]-2,3,4,2',3',4'-hexabenzyl-α,α'-trehalose (150 mg, 95.5 μmol) obtained in Production Example E-6 was used.

[α]$_D$$^{20}$ +60.5° (c 1.2 MeOH)

FT-IR (neat) 3366, 2926, 2856, 1731 cm$^{-1}$ $^1$H-NMR (300 MHz in CD$_3$OD) δ0.85 (6H, t, J=6.7 Hz), 0.86 (6H, t, J=7.1 Hz), 1.12-1.64 (44H, m), 2.39 (2H, ddd, J=10.4 Hz, 6.1 Hz, 3.0 Hz), 3.30 (2H, dd, J=10.0 Hz, 9.8 Hz), 3.43 (2H, dd, J=9.8 Hz, 3.7 Hz), 3.64 (2H, m), 3.74 (2H, t, J=9.8 Hz), 3.99 (2H, ddd, J=10.0 Hz, 5.4 Hz, 2.1 Hz), 4.15 (2H, dd, J=10.1 Hz, 5.4 Hz), 4.38 (2H, dd, J=10.1 Hz, 2.1 Hz), 5.01 (2H, d, J=3.7 Hz)

$^{13}$C-NMR (75 MHz in CD$_3$OD) δ14.5, 23.7 (2C), 26.6, 28.6, 29.9, 30.3, 30.4, 30.7, 32.8, 33.0, 35.6, 54.2, 64.3, 71.5, 72.0, 73.2, 73.6, 74.4, 95.3, 176.2

FABMS m/z (%) 874 (50 M$^+$+Na), 619 (8), 457 (8), 255 (15), 169 (10), 145 (10), 127 (20), 97 (30), 83 (50), 69 (89), 55 (100)

HRMS (FAB$^+$) m/z Calculation Value: C$_{44}$H$_{82}$O$_{15}$Na (M$^+$+Na) 873.5551, Actual Measurement Value: 873.5533

Production Example F-7

Production of 6,6'-bis-O-[(2R,3R)-3-methoxy-2-pentylnonanoyl]-α,α'-trehalose

The target compound (102 mg, 89%) was obtained in the same manner as in Production Example F-1, except that the 6,6'-bis-O-[(2R,3R)-3-methoxy-2-pentylnonanoyl]-2,3,4,2',3',4'-hexabenzyl-α,α'-trehalose (189 mg, 139 μmol) obtained in Production Example E-7 was used.

[α]$_D$$^{20}$ +92.3° (c 4.6 MeOH)

FT-IR (neat) 3298, 2955, 2930, 2859, 1743 cm$^{-1}$ $^1$H-NMR (300 MHz in CD$_3$OD) δ0.85 (12H, m), 1.14-1.64 (36H, m), 2.57 (2H, ddd, J=10.5 Hz, 7.0 Hz, 3.4 Hz), 3.27 (6H, s), 3.30 (2H, m), 3.38 (2H, m), 3.42 (2H, dd, J=9.8 Hz, 3.7 Hz), 3.75 (2H, t, J=9.4 Hz), 3.99 (2H, ddd, J=10.2 Hz, 5.1 Hz, 1.9 Hz), 4.17 (2H, dd, J=11.8 Hz, 5.1 Hz), 4.34 (2H, dd, J=11.8 Hz, 1.9 Hz), 5.01 (2H, d, J=3.7 Hz)

$^{13}$C-NMR (75 MHz in CD$_3$OD) δ14.5 (2C), 23.5, 23.6, 25.8, 28.4, 28.5, 28.7, 30.5, 31.6, 32.9 (2C), 50.8, 57.9, 64.4, 71.3, 71.9, 73.1, 74.5, 83.4, 95.1, 175.9

FABMS m/z (%) 846 (100 M$^+$+Na), 844 (10), 587 (5), 443 (8), 303 (12), 241 (18)

HRMS (FAB$^+$) m/z Calculation Value: C$_{42}$H$_{78}$O$_{15}$Na (M$^+$+Na) 845.5239, Actual Measurement Value: 845.5253

Production Example F-8

Production of 6,6'-bis-O-(2-butylhexanoyl)-α,α'-trehalose

The target compound (99.5 mg, 91%) was obtained in the same manner as in Production Example F-1, except that the 6,6'-bis-O-(2-butylhexanoyl)-2,3,4,2',3',4'-hexabenzyl-α,α'-trehalose (200 mg, 168 μmol) obtained in Production Example E-8 was used.

[α]$_D$$^{20}$ +108.4° (c 1.0 MeOH)

FT-IR (neat) 3341, 2958, 2861, 1744 cm$^{-1}$ $^1$H-NMR (300 MHz in CD$_3$OD) δ0.85 (12H, t, J=7.0 Hz), 1.25 (16H, m), 1.43 (4H, m), 1.55 (4H, m), 2.32 (2H, m), 3.30 (2H, m), 3.41 (2H, dd, J=9.1 Hz, 3.7 Hz), 3.75 (2H, t, J=9.1 Hz), 3.97 (2H, ddd, J=9.9 Hz, 5.1 Hz, 2.1 Hz), 4.16 (2H, dd, J=11.8 Hz, 5.1 Hz), 4.35 (2H, dd, J=11.8 Hz, 2.1 Hz), 5.01 (2H, d, J=3.7 Hz)

$^{13}$C-NMR (75 MHz in CD$_3$OD) δ14.3, 23.6, 30.6, 30.7, 33.3 (2C), 47.0, 64.1, 71.4, 71.9, 73.1, 74.5, 95.0, 178.0

FABMS m/z (%) 673 (100 M$^+$+Na), 629 (5), 573 (5), 501 (5), 317 (6), 299 (4), 173 (4)

HRMS (FAB$^+$) m/z Calculation Value: C$_{32}$H$_{58}$O$_{13}$Na (M$^+$+Na) 673.3776, Actual Measurement Value: 673.3795

Production Example F-9

Production of 6,6'-bis-O-(2-pentylheptanoyl)-α,α'-trehalose

The target compound (111 mg, 89%) was obtained in the same manner as in Production Example F-1, except that the 6,6'-bis-O-(2-pentylheptanoyl)-2,3,4,2',3',4'-hexabenzyl-α,α'-trehalose (220 mg, 176 μmol) obtained in Production Example E-9 was used.

[α]$_D$$^{20}$ +97.5° (c 5.2 MeOH)

FT-IR (neat) 3308, 2932, 2859, 1746 cm$^{-1}$ $^1$H-NMR (300 MHz in CD$_3$OD) δ0.85 (12H, t, J=6.5 Hz), 1.24 (24H, m), 1.42 (4H, m), 1.54 (4H, m), 2.32 (2H, m), 3.29 (2H, m), 3.41 (2H, dd, J=9.8 Hz, 3.9 Hz), 3.74 (2H, t, J=9.8 Hz), 3.97 (2H, ddd, J=9.8 Hz, 5.0 Hz, 1.8 Hz), 4.16 (2H, dd, J=12.0 Hz, 5.0 Hz), 4.33 (2H, dd, J=12.0 Hz, 1.8 Hz), 5.01 (2H, d, J=3.7 Hz)

$^{13}$C-NMR (75 MHz in CD$_3$OD) δ14.4, 23.5, 28.1, 28.2, 32.9, 33.6, 47.1, 64.2, 71.4, 71.9, 73.1, 74.5, 95.0, 178.0

FARMS m/z (%) 729 (100 M$^+$+Na), 727 (10), 671 (6), 529 (6), 345 (7), 155 (10)

HRMS (FAB$^+$) m/z Calculation Value: C$_{36}$H$_{66}$O$_{13}$Na (M$^+$+Na) 729.4401, Actual Measurement Value: 729.4410

Production Example F-10

Production of 6,6'-bis-O-(2-hexyloctanoyl)-α,α'-trehalose

The target compound (101 mg, 85%) was obtained in the same manner as in Production Example F-1, except that the 6,6'-bis-O-(2-hexyloctanoyl)-2,3,4,2',3',4'-hexabenzyl-α,α'-trehalose (202 mg, 155 μmol) obtained in Production Example E-10 was used.

[α]$_D$$^{20}$ +90.3° (c 4.2 MeOH)

FT-IR (neat) 3296, 2927, 2857, 1742 cm$^{-1}$ $^1$H-NMR (300 MHz in CD$_3$OD) δ0.85 (12H, t, J=6.9 Hz), 1.24 (32H, m), 1.42 (4H, m), 1.54 (4H, m), 2.32 (2H, m), 3.29 (2H, m), 3.41 (2H, dd, J=9.8 Hz, 3.7 Hz), 3.74 (2H, t, J=9.8 Hz), 3.97 (2H, ddd, J=10.0 Hz, 5.2 Hz, 2.0 Hz), 4.16 (2H, dd, J=12.0 Hz, 5.2 Hz), 4.32 (2H, dd, J=12.0 Hz, 2.0 Hz), 5.01 (2H, d, J=3.7 Hz)

$^{13}$C-NMR (75 MHz in CD$_3$OD) δ14.5, 23.7, 28.4, 28.5, 30.3, 32.8, 33.6, 47.1, 64.2, 71.4, 71.9, 73.1, 74.5, 95.0, 178.0

FABMS m/z (%) 786 (100 M$^+$+Na), 784 (11), 713 (7), 557 (7), 413 (5), 165 (6)

HRMS FAB$^+$) m/z Calculation Value: C$_{40}$H$_{74}$O$_{13}$Na (M$^+$+Na) 785.5027, Actual Measurement Value: 785.5057

Production Example F-11

Production of 6,6'-bis-O-(2-pentylnonanoyl)-α,α'-trehalose

The target compound (119 mg, 88%) was obtained in the same manner as in Production Example F-1, except that the 6,6'-bis-O-(2-pentylnonanoyl)-2,3,4,2',3',4'-hexabenzyl-α,α'-trehalose (230 mg, 177 µmol) obtained in Production Example E-11 was used.

$[\alpha]_D^{20}$ +88.7° (c 3.6 MeOH)
FT-IR (neat) 3311, 2928, 2857, 1742 cm$^{-1}$
$^1$H-NMR (300 MHz in CD$_3$OD) δ0.85 (12H, t, J=7.2 Hz), 1.24 (32H, m), 1.42 (4H, m), 1.54 (4H, m), 2.32 (2H, m), 3.29 (2H, t, J=9.5 Hz), 3.41 (2H, dd, J=9.5 Hz, 3.7 Hz), 3.74 (2H, t, J=9.5 Hz), 3.97 (2H, ddd, J=9.5 Hz, 5.2 Hz, 1.9 Hz), 4.16 (2H, dd, J=12.0 Hz, 5.2 Hz), 4.33 (2H, dd, J=12.0 Hz, 1.9 Hz), 5.01 (1H, d, J=3.7 Hz)
$^{13}$C-NMR (75 MHz in CD$_3$OD) δ14.4, 14.5, 23.6, 23.7, 28.2 (2C), 28.5 (2C), 30.3, 30.6, 33.0 (2C), 33.6, 47.1, 64.2, 71.4, 72.0, 73.2, 74.6, 95.0, 178.1
FABMS m/z (%) 786 (100 M$^+$+Na), 784 (10), 557 (5), 413 (5), 373 (6), 183 (10)
HRMS (FAB$^+$) m/z Calculation Value: C$_{40}$H$_{74}$O$_{13}$Na (M$^+$+Na) 785.5027, Actual Measurement Value: 785.5021

Production Example F-12

Production of 6-O-[(2R,3R)-2-butyl-3-hydroxyoctanoyl]-6'-O-[(2S,3S)-2-butyl-3-hydroxyoctanoyl]-α,α'-trehalose The target compound (53.3 mg, 81%) was obtained in the same manner as in Production Example F-1, except that the 6-O-[(2R,3R)-3-benzyloxy-2-butyloctanoyl]-6'-O-[(2S,3S)-3-benzyloxy 2-butyloctanoyl]-2,3,4,2',3',4'-hexabenzyl-α,α'-trehalose (130 mg, 89.1 µmol) obtained in Production Example E-12-2 was used.

$[\alpha]_D^{20}$ +97.1° (c 4.8)
FT-IR (neat) 3390, 2955, 2932, 2860, 1718 cm$^{-1}$
$^1$H-NMR (300 MHz in CD$_3$OD) δ0.91 (12H, m), 1.20-1.69 (28H, m), 2.43 (2H, m), 3.35 (2H, m), 3.46 (1H, dd, J=9.8 Hz, 3.7 Hz), 3.47 (1H, dd, J=9.8 Hz, 3.7 Hz), 3.67 (2H, m), 3.78 (2H, m), 4.04 (2H, m), 4.19 (1H, dd, J=11.8 Hz, 5.5 Hz), 4.20 (1H, dd, J=11.8 Hz, 5.8 Hz), 4.43 (2H, m), 5.05 (1H, d, J=3.7 Hz), 5.06 (1H, d, J=3.7 Hz)
$^{13}$C-NMR (75 MHz in CD$_3$OD) δ14.3, 14.4, 23.6 (2C), 23.7, 26.2, 26.3, 29.5, 30.8 (2C), 32.9, 35.5, 54.1 (2C), 64.2, 64.4, 71.4, 71.5, 71.8, 72.0, 73.0, 73.1, 73.5, 73.6, 74.3, 95.4, 176.2 (2C)
FABMS m/z (%) 761 (13 M$^+$+Na), 307 (14), 289 (10), 154 (100), 136 (80), 89 (25)
HRMS (FAB$^+$) m/z Calculation Value: C$_{36}$H$_{66}$O$_{15}$Na (M$^+$+Na) 761.4300, Actual Measurement Value: 761.4277

Production Example F-13

Production of 6-O-[(2R,3R)-3-hydroxy-2-pentylnonanoyl]-6'-O-[(2S,3S)-3-hydroxy-2-pentylnonanoyl]-α,α'-trehalose The target compound (44.4 mg, 77%) was obtained in the same manner as in Production Example F-1, except that the 6-O-[(2R,3R)-3-benzyloxy-2-pentylnonanoyl]-6'-O-[(2S,3S)-3-benzyloxy-2-pentylnonanoyl]-2,3,4,2',3',4'-hexabenzyl-α,α'-trehalose (110 mg, 72.6 µmol) obtained in Production Example E-13-2 was used.

$[\alpha]_D^{20}$ +84.5° (c 1.2 MeOH)
FT-IR (neat) 3374, 2928, 2858, 1716 cm$^{-1}$
$^1$H-NMR (600 MHz in C$_5$D$_5$N) δ0.82 (12H, m), 1.23 (20H, m), 1.38 (2H, m), 1.43 (2H, m), 1.52 (4H, m), 1.63-1.83 (6H, m), 1.92 (2H, m), 2.86 (2H, ddd, J=11.0 Hz, 7.4 Hz, 4.1 Hz), 4.17 (4H, m), 4.26 (2H, m), 4.70 (1H, t, J=8.8 Hz), 4.71 (1H, t, J=9.1 Hz), 4.80 (1H, dd, J=11.8 Hz, 5.2 Hz), 4.86 (1H, dd, J=12.1 Hz, 5.8 Hz), 5.08 (2H, ddd, J=10.2 Hz, 4.9 Hz, 2.2 Hz), 5.15 (2H, m), 5.21 (1H, dd, J=10.2 Hz, 1.9 Hz), 5.85 (1H, d, J=3.6 Hz), 5.86 (1H, d, J=3.6 Hz), 6.25 (OH, d, J=6.3 Hz), 6.31 (OH, d, J=6.6 Hz), 7.03 (OH, m), 7.24 (OH, br s), 7.27 (OH, br s)
$^{13}$C-NMR (150 MHz in C$_5$D$_5$N) δ14.2 (2C), 22.7, 22.9, 26.1, 26.2, 27.7, 27.8, 29.3, 29.7, 32.1 (2C), 32.2, 35.4, 53.9, 54.1, 63.9, 64.2, 71.6, 71.7, 72.1, 72.2, 72.4, 72.5, 73.3, 73.4, 74.7, 95.9, 111.6, 175.1, 175.2
FABMS m/z (%) 818 (100), 817 (3 M$^+$+Na), 816 (13), 645 (4), 591 (5), 499 (5), 429 (7), 289 (5), 227 (12), 55 (69)
HRMS (FAB$^+$) m/z Calculation Value: C$_{40}$H$_{74}$O$_{15}$Na (M$^+$+Na) 817.4925, Actual Measurement Value: 817.4906

Production Example F-14

Production of 6-O-[(2R,3R)-3-hydroxy-2-hexyldecanoyl]-6'-O-[(2S,3S)-3-hydroxy-2-hexyldecanoyl]-α,α'-trehalose The target compound (44.7 mg, 81%) was obtained in the same manner as in Production Example F-1, except that the 6-O-[(2R,3R)-3-benzyloxy-2-hexyldecanoyl]-6'-O-[(2S,3S)-3-benzyloxy 2-hexyldecanoyl]-2,3,4,2',3',4'-hexabenzyl-α,α'-trehalose (102 mg, 64.9 µmol) obtained in Production Example E-14-2 was used.

$[\alpha]_D^{20}$ +89.1° (c 0.8 MeOH)
FT-IR (neat) 3364, 2927, 2857, 1732 cm$^{-1}$
$^1$H-NMR (300 MHz in CD$_3$OD) δ0.90 (12H, t, J=5.9 Hz), 1.16-1.70 (44H, m), 2.44 (2H, ddd, J=11.4 Hz, 6.9 Hz, 4.0 Hz), 3.35 (2H, m), 3.46 (1H, dd, J=9.8 Hz, 3.6 Hz), 3.47 (1H, dd, J=9.6 Hz, 3.6 Hz), 3.68 (2H, m), 3.78 (2H, t, J=9.8 Hz), 4.04 (1H, m), 4.09 (1H, m), 4.19 (1H, dd, J=11.8 Hz, 5.2 Hz), 4.20 (1H, dd, J=11.8 Hz, 5.2 Hz), 4.42 (1H, dd, J=11.8 Hz, 2.5 Hz), 4.43 (1H, dd, J=11.8 Hz, 2.5 Hz), 5.05 (1H, d, J=3.6 Hz), 5.06 (1H, d, J=3.6 Hz)
$^{13}$C-NMR (75 MHz in CD$_3$OD) δ14.5, 23.7 (2C), 26.6, 26.7, 28.5, 28.6, 29.8, 30.3, 30.4, 30.7, 32.8, 33.0, 35.6, 54.2 (2C), 64.3, 64.5, 71.4, 71.5, 71.9, 72.1, 73.1, 73.2, 73.6 (2C), 74.4, 95.4, 176.2 (2C)
FABMS m/z (%) 874 (60 M$^+$+Na), 744 (5), 674 (5), 619 (8), 485 (6), 457 (8), 255 (19), 169 (10), 127 (20), 55 (100)
HRMS (FAB$^+$) m/z Calculation Value: C$_{44}$H$_{82}$O$_{15}$Na (M$^+$+Na) 873.5551, Actual Measurement Value: 873.5526

Production Example F-15

Production of 6,6'-bis-N-[(2R,3R)-3-hydroxy-2-pentylnonanoylamino]-6,6'-dideoxy-α,α'-trehalose The target compound (86.9 mg, 83%) was obtained in the same manner as in Production Example F-1, except that the 6,6'-bis-N-[(2R,3R)-3-benzyloxy-2-pentylnonanoylamino]-6,6'-dideoxy-2,3,4,2',3',4'-hexabenzyl-α,α'-trehalose (200 mg, 132 µmol) obtained in Production Example E-15 was used.

$[\alpha]_D^{20}$ +85.6° (c 1.8 MeOH)
FT-IR (neat) 3357, 2930, 2858, 1634, 1556 cm$^{-1}$
$^1$H-NMR (300 MHz in CD$_3$OD) δ0.86 (12H, t, J=6.1 Hz), 1.14-1.64 (36H, m), 2.18 (2H, dt, J=10.0 Hz, 4.8 Hz), 3.10 (2H, t, J=9.8 Hz), 3.34 (2H, dd, J=14.0 Hz, 6.6 Hz), 3.40 (2H, dd, J=9.8 Hz, 3.6 Hz), 3.53 (2H, dd, J=14.0 Hz, 2.9 Hz), 3.58 (2H, m), 3.71 (2H, t, J=9.8 Hz), 3.89 (2H, ddd, J=10.0 Hz, 6.7 Hz, 2.9 Hz), 5.02 (2H, d, J=3.7 Hz)
$^{13}$C-NMR (75 MHz in CD$_3$OD) δ14.5, 23.6, 23.7, 26.7, 28.3, 30.4, 30.8, 33.0 (2C), 36.1, 41.4, 54.2, 72.0, 73.3, 73.5, 74.1, 95.8, 178.1

FABMS m/z (%) 816 (100 M$^+$+Na), 815 (5), 814 (12), 589 (5), 428 (10), 388 (12), 322 (4)
HRMS (FAB$^+$) m/z Calculation Value: C$_{40}$H$_{76}$O$_{13}$N$_2$Na (M$^+$+Na) 815.5245, Actual Measurement Value: 815.5226

Production Example F-16

Production of 6,6'-bis-N-[(2R,3R)-3-methoxy-2-pentylnonanoylamino]-6,6'-dideoxy-α,α'-trehalose The target compound (99.7 mg, 87%) was obtained in the same manner as in Production Example F-1, except that the 6,6'-bis-N-[(2R,3R)-3-methoxy-2-pentylnonanoylamino]-6,6'-dideoxy-2,3,4,2',3',4'-hexabenzyl-α,α'-trehalose (190 mg, 140 μmol) obtained in Production Example E-16 was used.
[α]$_D^{20}$ +59.7° (c 4.2 MeOH)
FT-IR (neat) 3347, 2929, 2858, 1644, 1550 cm$^{-1}$
$^1$H-NMR (300 MHz in CD$_3$OD) δ0.86 (12H, m), 1.12-1.68 (36H, m), 2.35 (2H, ddd, J=10.2 Hz, 6.9 Hz, 3.9 Hz), 3.12 (2H, t, J=9.1 Hz), 3.29 (6H, s), 3.38-3.52 (8H, m), 3.76 (2H, t, J=9.1 Hz), 3.84 (2H, ddd, J=9.2 Hz, 5.9 Hz, 3.0 Hz), 5.03 (2H, d, J=3.9 Hz)
$^{13}$C-NMR (75 MHz in CD$_3$OD) δ14.5, 23.6 (2C), 25.8, 28.3, 30.1, 30.6, 32.1, 32.9, 33.0, 41.5, 52.4, 58.6, 71.9, 73.3, 73.4, 74.1, 83.3, 95.5, 177.6
FABMS m/z (%) 844 (100 M$^+$+Na), 812 (3), 713 (3), 470 (3), 442 (10), 344 (9)
HRMS (FAB$^+$) m/z Calculation Value: C$_{42}$H$_{80}$O$_{13}$N$_2$Na (M$^+$+Na) 843.5558, Actual Measurement Value: 843.5537

Production Example F-17

Production of 6,6'-bis-N-(2-hexyloctanoylamino)-6,6'-dideoxy-α,α'-trehalose

The target compound (97.6 mg, 83%) was obtained in the same manner as in Production Example F-1, except that the 6,6'-bis-N-(2-hexyloctanoylamino)-6,6'-dideoxy-2,3,4,2',3',4'-hexabenzyl-α,α'-trehalose (201 mg, 154 μmol) obtained in Production Example E-17 was used.
[α]$_D^{20}$ +55.7° (c 1.0 MeOH)
FT-IR (neat) 3358, 2936, 2858, 1645, 1539 cm$^{-1}$
$^1$H-NMR (300 MHz in CD$_3$OD) δ0.85 (12H, t, J=6.7 Hz), 1.24 (32H, m), 1.35 (4H, m), 1.50 (4H, m), 2.17 (2H, m), 3.11 (2H, t, J=9.1 Hz), 3.34 (2H, m), 3.40 (2H, dd, J=9.1 Hz, 3.7 Hz), 3.52 (2H, m), 3.76 (2H, t, J=9.1 Hz), 3.84 (2H, ddd, J=9.1 Hz, 5.5 Hz, 2.9 Hz), 5.00 (2H, d, J=3.7 Hz), 7.83 (NH, br t, J=6.2 Hz)
$^{13}$C-NMR (75 MHz in CD$_3$OD) δ14.5, 23.7 (2C), 28.5, 28.7, 30.4 (2C), 32.8, 34.1, 41.2, 48.3, 72.0, 73.1, 73.3, 74.0, 95.5, 179.8
FABMS m/z (%) 784 (100 M$^+$+Na), 627 (7), 412 (11), 372 (12), 354 (6), 105 (19)
HRMS (FAB$^+$) m/z Calculation Value: C$_{40}$H$_{76}$O$_{11}$N$_2$Na (M$^+$+Na) 783.5347, Actual Measurement Value: 783.5353

Production Example F-18

Production of 6,6'-bis-N-(2-pentylnonanoylamino)-6,6'-dideoxy-α,α'-trehalose

The target compound (96.8 mg, 79%) was obtained in the same manner as in Production Example F-1, except that the 6,6'-bis-N-(2-pentylnonanoylamino)-6,6'-dideoxy-2,3,4,2',3',4'-hexabenzyl-α,α'-trehalose (210 mg, 161 μmol) obtained in Production Example E-18 was used.
[α]$_D^{20}$ +54.6° (c 5.3 MeOH)
FT-IR (neat) 3328, 2929, 2857, 1644, 1549 cm$^{-1}$
$^1$H-NMR (300 MHz in CD$_3$OD) δ0.85 (12H, m), 1.24 (36H, m), 1.50 (4H, m), 2.17 (2H, m), 3.11 (2H, t, J=9.6 Hz), 3.35 (2H, m), 3.40 (2H, dd, J=9.6 Hz, 3.7 Hz), 3.52 (2H, m), 3.75 (2H, t, J=9.6 Hz), 3.84 (2H, ddd, J=9.6 Hz, 5.4 Hz, 2.9 Hz), 5.01 (2H, d, J=3.7 Hz)
$^{13}$C-NMR (75 MHz in CD$_3$OD) δ14.5, 23.5, 23.6, 23.7, 28.3, 28.4, 28.6, 28.7, 30.3, 30.7, 33.0, 34.1, 41.1, 48.2, 72.0, 73.1, 73.4, 74.0, 95.5, 179.7
FABMS m/z (%) 784 (100 M$^+$+Na), 627 (5), 412 (10), 372 (9), 344 (2)
HRMS (FAB$^+$) m/z Calculation Value: C$_{40}$H$_{76}$O$_{11}$N$_2$Na (M$^+$+Na) 783.5346, Actual. Measurement Value: 783.5364

Test Example 1

Test for Affinity for Adenosine A3 Receptor

The adenosine A3 receptor affinity of the trehalose compounds obtained in Production Examples F-1 to 18 were measured according to the adenosine A1 receptor binding experiment procedure disclosed in Molecular Pharmacology, volume 53, pages 886-893, (1998).

Specifically, ovarium K1 cells of a Chinese hamster (obtained from Euroscreen S. A.; hereunder referred to as "CHO-K1") expressing human recombinant adenosine A3 receptors were cultured in a modified HEPES buffer free of Ca$^{2+}$ and Mg$^{2+}$. Subsequently, the cultured CHO-K1 was scraped and homogenized in 50 mM of ice-cooled Tris-HCl (pH 7.4). The resulting mixture was subjected to centrifugation at 48,000×g for 15 minutes to obtain a cell membrane pellet. The obtained cell membrane pellet was washed twice with another modified HEPES buffer, and then subjected again to centrifugation. The washed cell membrane pellet was suspended again in a small quantity of 50 mM Tris-HCl (pH 7.4).

The concentration of the adenosine A3 receptor in the obtained cell membrane pellet was measured as follows. A 0.5 nM amount of [$^{125}$I] AB-MECA (a selective radioligand of A3/A1 receptor (N$^6$-(4-amino-3-iodobenzyl)-5'-(N-methoxy carbamoyl) adenosine)) was added to 20 μL of the obtained suspension of the aforesaid cell membrane pellet (containing 2 μg of protein), which was then subjected to incubation for 60 minutes at 25° C. Thereafter, 50 mM of ice-cooled Tris-HCl (pH 7.4) was added thereto to halt the reaction, and then the cell membrane pellet was filtrated out using a glass fiber filter. The filtered cell membrane pellet was washed 3 times with an ice-cooled buffer so as to remove excessive ligands. The radioactivity in the resulting cell membrane pellet on a filter was measured using a scintillation counter (Type 1470 Automatic Counter; PerkinElmer, Inc.).

Separately, in order to measure nonspecific bindings of [$^{125}$I] AB-MECA other than to an adenosine A3 receptor, 1 μM of [$^{125}$I] IB-MECA (a selective radioagonist of A3 receptor N$^6$-(3-iodobenzyl)-5'-(N-methoxycarbamoyl) adenosine) was further added to the obtained suspension of the cell membrane pellet, and the same measurement was carried out as in the aforesaid binding experiment. The average specific binding value of [$^{125}$I] AB-MECA to the adenosine A3 receptor was calculated based on the results obtained in the above experiment. The calculated results are shown below.

Kd: 5.9 nM
Bmax: 1800 fmol/mg protein
Specific binding: 83%

The adenosine A3 receptor affinity of each trehalose compound obtained in Production Examples F-1 to 18 was calculated based on the results of the same measurement carried out with respect to the suspension of the aforesaid cell membrane pellet to which 3 μM or 10μ of each trehalose compound had been added. Further, in a Comparative Example, the same measurement was carried out with respect to the compounds taught in Non-Patent Document 1 and Non-Patent Document 2 (in the chemical formula of Table 1, R$^1$=R$^3$=octyl, R$^2$=R$^4$=heptyl, X=X'=OH, and Y=Y'=O). The results are shown in Table 1.

TABLE 1

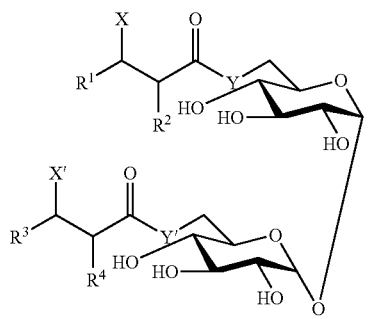

| Production Example | R¹ | R² | R³ | R⁴ | X | Y | X' | Y' | Absolute Stereochemistry 2,3,2',3' position | Affinity 3 μM | 10 μM | IC$_{50}$ |
|---|---|---|---|---|---|---|---|---|---|---|---|---|
| F-1 | hexyl | pentyl | hexyl | pentyl | OH | O | OH | O | RRRR | 56 | 97 | 2.61 μM |
| F-2 | hexyl | pentyl | hexyl | pentyl | OH | O | OH | O | SSSS | 57 | 86 | |
| F-3 | hexyl | pentyl | hexyl | pentyl | OH | O | OH | O | RSRS | 59 | 100 | |
| F-4 | hexyl | pentyl | hexyl | pentyl | OH | O | OH | O | SRSR | 32 | 91 | |
| F-5 | heptyl | hexyl | heptyl | hexyl | OH | O | OH | O | RRRR | ND | 83 | |
| F-6 | heptyl | hexyl | heptyl | hexyl | OH | O | OH | O | SSSS | ND | 59 | |
| F-7 | hexyl | pentyl | hexyl | pentyl | OMe | O | OMe | O | RRRR | 84 | 96 | |
| F-8 | propyl | butyl | propyl | butyl | H | O | H | O | | 14 | 72 | |
| F-9 | butyl | pentyl | butyl | pentyl | H | O | H | O | | 97 | 99 | 0.459 μM |
| F-10 | pentyl | hexyl | pentyl | hexyl | H | O | H | O | | 65 | 66 | |
| F-11 | hexyl | pentyl | hexyl | pentyl | H | O | H | O | | 74 | 62 | |
| F-12 | pentyl | butyl | pentyl | butyl | OH | O | OH | O | RRSS | ND | 48 | |
| F-13 | hexyl | pentyl | hexyl | pentyl | OH | O | OH | O | RRSS | 54 | 97 | 2.75 μM |
| F-14 | heptyl | hexyl | heptyl | hexyl | OH | O | OH | O | RRSS | ND | 77 | |
| F-15 | hexyl | pentyl | hexyl | pentyl | OH | NH | OH | NH | RRRR | 29 | 69 | |
| F-16 | hexyl | pentyl | hexyl | pentyl | OMe | NH | OMe | NH | RRRR | 57 | 96 | |
| F-17 | pentyl | hexyl | pentyl | hexyl | H | NH | H | NH | | 22 | ND | |
| F-18 | hexyl | pentyl | hexyl | pentyl | H | NH | H | NH | | 33 | 89 | |
| Comparative Example | octyl | heptyl | octyl | heptyl | OH | O | OH | O | RRSS | ND | 29 | |

The results above clearly show that the trehalose compounds of the present invention exhibit a high affinity for an adenosine A3 receptor, while known trehalose compounds exhibit a low affinity for an adenosine A3 receptor. Accordingly, it is proved that the trehalose compound of the present invention exhibits a remarkably higher affinity for an adenosine A3 receptor than known trehalose compounds.

The invention claimed is:

1. A trehalose compound represented by General Formula (1):

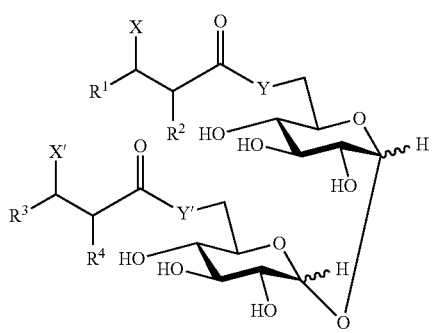

(1)

wherein X and X' are the same or different, and each represent a hydrogen atom, a hydroxy group, or a $C_1$-$C_6$ alkoxy group;

Y and Y' are the same or different, and each represent an oxygen atom or —NR$^5$— wherein R$^5$ represents a hydrogen atom or a $C_1$-$C_6$ alkyl group;

R¹ and R³ each represent a $C_1$-$C_7$ alkyl group; and

R² and R⁴ each represent a $C_3$-$C_6$ alkyl group.

2. The trehalose compound according to claim 1, wherein X and X' are both hydrogen atoms.

3. The trehalose compound according to claim 1, wherein X and X' are both hydroxy groups.

4. The trehalose compound according to claim 1, wherein X and X' are both methoxy groups.

5. The trehalose compound according to claim 4, wherein Y and Y' are both oxygen atoms.

6. The trehalose compound according to claim 4, wherein Y and Y' are both —NH—.

7. The trehalose compound according to claim 6, wherein R¹ and R³ are both n-hexyl groups.

8. The trehalose compound according to claim 6, wherein R² and R⁴ are both n-pentyl groups.

9. The trehalose compound according to claim 1, which is selected from the group consisting of:

6,6'-bis-N-(2-pentylnonanoylamino)-6,6'-dideoxy-α,α'-trehalose;

6,6'-bis-O-(2-pentylheptanoyl)-α,α'-trehalose;

6,6'-bis-N-[(2R,3R)-3-methoxy-2-pentyl-nonanolyamino]-6,6'-dideoxy-α,α'-trehalose;

6,6'-bis-O-[(2R,3R)-3-methoxy-2-pentylnonanoyl]-α,α'-trehalose;

6,6'-bis-O-[(2R,3S)-3-hydroxy-2-pentylnonanoyl]-α,α'-trehalose;

6,6'-bis-O-[(2R,3R)-3-hydroxy-2-pentylnonanoyl]-α,α'-trehalose;

6,6'-bis-O-[(2S,3S)-3-hydroxy-2-pentylnonanoyl]-α,α'-trehalose;

6-O-[(2R,3R)-3-hydroxy-2-pentylnonanoyl]-6'-O-[(2S,3S)-3-hydroxy-2-pentylnonanoyl]-α,α'-trehalose; and 6,6'-bis-O-[(2S,3R)-3-hydroxy-2-pentylnonanoyl]-α,α'-trehalose.

10. A pharmaceutical composition comprising the trehalose compound according to claim 1.

11. An adenosine A3 receptor antagonist composition comprising the trehalose compound according to claim 1.

* * * * *